US009259339B1

(12) United States Patent
Yan et al.

(10) Patent No.: US 9,259,339 B1
(45) Date of Patent: Feb. 16, 2016

(54) BIODEGRADABLE ENDOPROSTHESES AND METHODS OF THEIR FABRICATION

(71) Applicant: Elixir Medical Corporation, Sunnyvale, CA (US)

(72) Inventors: John Yan, Los Gatos, CA (US); Vinayak Bhat, Cupertino, CA (US)

(73) Assignee: ELIXIR MEDICAL CORPORATION, Sunnyvale, CA (US)

( * ) Notice: Subject to any disclaimer, the term of this patent is extended or adjusted under 35 U.S.C. 154(b) by 0 days.

(21) Appl. No.: 14/682,014

(22) Filed: Apr. 8, 2015

Related U.S. Application Data

(63) Continuation-in-part of application No. 14/461,159, filed on Aug. 15, 2014, now Pat. No. 9,119,905.

(51) Int. Cl.
*A61F 2/06* (2013.01)
*A61F 2/89* (2013.01)

(52) U.S. Cl.
CPC ........... *A61F 2/89* (2013.01); *A61F 2210/0004* (2013.01); *A61F 2230/0069* (2013.01)

(58) Field of Classification Search
CPC ............... A61F 2/07; A61F 2/01; A61F 2/06; A61F 2/82–2/958; A61F 2002/018; A61F 2002/06; A61F 2002/07; A61F 2002/30062; A61F 2002/30064; A61F 2002/30112; A61F 2002/82; A61F 2002/825; A61F 2002/91
USPC ................................................ 623/1.38–1.48
See application file for complete search history.

(56) References Cited

U.S. PATENT DOCUMENTS

| | | | |
|---|---|---|---|
| 3,867,190 A | 2/1975 | Schmitt et al. | |
| 5,298,276 A | 3/1994 | Jayaraman | |
| 5,441,483 A | 8/1995 | Avitall | |
| 5,447,724 A | 9/1995 | Helmus et al. | |
| 5,500,013 A * | 3/1996 | Buscemi et al. | 623/1.22 |
| 5,670,161 A | 9/1997 | Healy et al. | |
| 5,674,286 A | 10/1997 | D'Alessio et al. | |
| 5,741,329 A | 4/1998 | Agrawal et al. | |
| 5,902,333 A | 5/1999 | Roberts et al. | |
| 5,935,119 A | 8/1999 | Guy et al. | |
| 5,957,975 A | 9/1999 | Lafont et al. | |
| 5,964,798 A | 10/1999 | Imran | |
| 5,980,564 A | 11/1999 | Stinson | |
| 6,027,526 A | 2/2000 | Limon et al. | |

(Continued)

FOREIGN PATENT DOCUMENTS

| | | |
|---|---|---|
| CN | 1328853 A | 1/2002 |
| CN | 1569270 A | 1/2005 |

(Continued)

OTHER PUBLICATIONS

Bae, et al. Drug delivery. Fundamentals and methods of tissue engineering. From 'Frontiers in Tissue Engineering' edited by Patrick et al. Feb. 20, 1998; Ch II.14:263-272.

(Continued)

*Primary Examiner* — Alvin Stewart
(74) *Attorney, Agent, or Firm* — Wilson, Sonsini, Goodrich & Rosati

(57) ABSTRACT

A biodegradable stent prosthesis formed from a degradable polymeric material, having a plurality of luminal, abluminal, and side surfaces, where at least some of the abluminal surfaces are concave and optionally the side surfaces are convex.

42 Claims, 7 Drawing Sheets

(56) References Cited

U.S. PATENT DOCUMENTS

| | | | |
|---|---|---|---|
| 6,039,755 A | 3/2000 | Edwin et al. | |
| 6,120,847 A | 9/2000 | Yang et al. | |
| 6,190,405 B1 | 2/2001 | Culombo et al. | |
| 6,224,803 B1 | 5/2001 | Tiernan | |
| 6,245,103 B1 | 6/2001 | Stinson | |
| 6,322,847 B1 | 11/2001 | Zhong et al. | |
| 6,323,256 B1 | 11/2001 | Delmain | |
| 6,395,326 B1* | 5/2002 | Castro et al. | 427/2.24 |
| 6,547,814 B2* | 4/2003 | Edwin et al. | 623/1.13 |
| 6,585,755 B2 | 7/2003 | Jackson et al. | |
| 6,626,939 B1 | 9/2003 | Burnside et al. | |
| 6,652,582 B1 | 11/2003 | Stinson | |
| 6,719,934 B2 | 4/2004 | Stinson | |
| 6,726,701 B2 | 4/2004 | Gilson et al. | |
| 6,761,784 B1 | 7/2004 | Hage | |
| 6,773,455 B2 | 8/2004 | Allen et al. | |
| 6,774,278 B1* | 8/2004 | Ragheb et al. | 623/1.1 |
| 6,776,796 B2 | 8/2004 | Falotico et al. | |
| 6,805,898 B1 | 10/2004 | Wu et al. | |
| 6,863,757 B1 | 3/2005 | Gonzalez et al. | |
| 6,896,695 B2 | 5/2005 | Mueller et al. | |
| 6,920,677 B2 | 7/2005 | Dolan et al. | |
| 6,997,948 B2 | 2/2006 | Stinson | |
| 7,001,421 B2* | 2/2006 | Cheng et al. | 623/1.11 |
| 7,108,716 B2 | 9/2006 | Burnside et al. | |
| 7,258,697 B1 | 8/2007 | Cox et al. | |
| 7,279,005 B2 | 10/2007 | Stinson | |
| 7,285,304 B1 | 10/2007 | Hossainy et al. | |
| 7,291,166 B2 | 11/2007 | Cheng et al. | |
| 7,329,366 B1 | 2/2008 | Gale et al. | |
| 7,354,450 B2 | 4/2008 | Bicek et al. | |
| 7,377,939 B2 | 5/2008 | Williams et al. | |
| 7,390,333 B2 | 6/2008 | Dutta | |
| 7,550,005 B2* | 6/2009 | Bates et al. | 623/1.15 |
| 7,563,277 B2 | 7/2009 | Case et al. | |
| 7,594,928 B2 | 9/2009 | Headley et al. | |
| 7,618,448 B2 | 11/2009 | Schmitz et al. | |
| 7,622,070 B2 | 11/2009 | Atladottir et al. | |
| 7,666,342 B2 | 2/2010 | Limon et al. | |
| 7,731,890 B2 | 6/2010 | Gale et al. | |
| 7,758,636 B2* | 7/2010 | Shanley et al. | 623/1.42 |
| 7,824,601 B1 | 11/2010 | Stankus et al. | |
| 7,829,008 B2 | 11/2010 | Gueriguian et al. | |
| 7,875,233 B2 | 1/2011 | Huang et al. | |
| 7,964,136 B2 | 6/2011 | Sabaria | |
| 7,967,998 B2 | 6/2011 | Gale et al. | |
| 7,971,333 B2 | 7/2011 | Gale et al. | |
| 8,057,534 B2* | 11/2011 | Boismier et al. | 623/1.38 |
| 8,172,897 B2 | 5/2012 | Gale et al. | |
| 8,182,890 B2 | 5/2012 | Zheng et al. | |
| 8,323,760 B2 | 12/2012 | Zheng et al. | |
| 8,425,587 B2 | 4/2013 | Trollsas et al. | |
| 8,501,079 B2 | 8/2013 | Glauser et al. | |
| 8,545,546 B2 | 10/2013 | Wang | |
| 8,562,670 B2* | 10/2013 | Pacetti et al. | 623/1.42 |
| 8,636,792 B2 | 1/2014 | Zheng et al. | |
| 8,709,071 B1* | 4/2014 | Huang et al. | 623/1.42 |
| 8,740,839 B2* | 6/2014 | Eaton et al. | 604/94.01 |
| 8,814,930 B2 | 8/2014 | Zheng et al. | |
| 8,834,556 B2 | 9/2014 | Papp et al. | |
| 8,852,263 B2 | 10/2014 | Wang | |
| 8,872,062 B2 | 10/2014 | Chen et al. | |
| 8,900,292 B2* | 12/2014 | Gregorich et al. | 623/1.42 |
| 8,956,403 B2* | 2/2015 | Gregorich et al. | 623/1.42 |
| 9,119,905 B2 | 9/2015 | Zheng et al. | |
| 2001/0016729 A1 | 8/2001 | Divino et al. | |
| 2001/0016769 A1 | 8/2001 | Hojeibane | |
| 2001/0016770 A1 | 8/2001 | Allen et al. | |
| 2001/0021871 A1 | 9/2001 | Stinson | |
| 2001/0053929 A1 | 12/2001 | Vonesh et al. | |
| 2002/0007209 A1* | 1/2002 | Scheerder et al. | 623/1.15 |
| 2002/0038146 A1* | 3/2002 | Harry | 623/1.16 |
| 2002/0161430 A1 | 10/2002 | Jang | |
| 2002/0183581 A1* | 12/2002 | Yoe et al. | 600/3 |
| 2002/0193336 A1 | 12/2002 | Elkins et al. | |
| 2003/0004563 A1 | 1/2003 | Jackson et al. | |
| 2003/0033007 A1 | 2/2003 | Sirhan et al. | |
| 2003/0050692 A1 | 3/2003 | Sirhan et al. | |
| 2003/0064097 A1 | 4/2003 | Patel et al. | |
| 2003/0088307 A1* | 5/2003 | Shulze et al. | 623/1.15 |
| 2003/0093143 A1 | 5/2003 | Zhao et al. | |
| 2003/0144726 A1 | 7/2003 | Majercak et al. | |
| 2003/0144729 A1 | 7/2003 | Bicek et al. | |
| 2003/0199993 A1 | 10/2003 | Gellman et al. | |
| 2003/0236320 A1 | 12/2003 | Martin et al. | |
| 2004/0006382 A1* | 1/2004 | Sohier | 623/1.15 |
| 2004/0073290 A1 | 4/2004 | Chouinard | |
| 2004/0199242 A1 | 10/2004 | Hong et al. | |
| 2005/0031704 A1 | 2/2005 | Ahn | |
| 2005/0060020 A1* | 3/2005 | Jenson | 623/1.13 |
| 2005/0070991 A1 | 3/2005 | Pienknagura | |
| 2005/0070996 A1* | 3/2005 | Dinh et al. | 623/1.42 |
| 2005/0075625 A1 | 4/2005 | Dao et al. | |
| 2005/0075716 A1 | 4/2005 | Yan | |
| 2005/0123588 A1 | 6/2005 | Zhu et al. | |
| 2005/0125051 A1 | 6/2005 | Eidenschink et al. | |
| 2005/0171595 A1* | 8/2005 | Feldman et al. | 623/1.15 |
| 2005/0187615 A1 | 8/2005 | Williams et al. | |
| 2005/0209680 A1 | 9/2005 | Gale et al. | |
| 2005/0216074 A1 | 9/2005 | Sahatjian et al. | |
| 2005/0232964 A1 | 10/2005 | Fennimore | |
| 2006/0025852 A1 | 2/2006 | Armstrong et al. | |
| 2006/0100695 A1 | 5/2006 | Peacock et al. | |
| 2006/0111485 A1 | 5/2006 | Laghi | |
| 2006/0122697 A1* | 6/2006 | Shanley et al. | 623/1.42 |
| 2006/0129222 A1 | 6/2006 | Stinson | |
| 2006/0136048 A1* | 6/2006 | Pacetti et al. | 623/1.42 |
| 2006/0147538 A1 | 7/2006 | Craig et al. | |
| 2006/0229711 A1 | 10/2006 | Yan et al. | |
| 2006/0251618 A1 | 11/2006 | Dennis et al. | |
| 2006/0265048 A1 | 11/2006 | Cheng et al. | |
| 2006/0271170 A1* | 11/2006 | Gale et al. | 623/1.49 |
| 2006/0287710 A1 | 12/2006 | Lendlein et al. | |
| 2007/0231365 A1 | 10/2007 | Wang et al. | |
| 2007/0253999 A1 | 11/2007 | Huang et al. | |
| 2007/0259099 A1 | 11/2007 | Van Sciver | |
| 2007/0271763 A1 | 11/2007 | Huang et al. | |
| 2007/0278720 A1 | 12/2007 | Wang et al. | |
| 2007/0281117 A1* | 12/2007 | Kaplan et al. | 428/35.7 |
| 2007/0290412 A1 | 12/2007 | Capek et al. | |
| 2007/0299505 A1 | 12/2007 | Gregorich et al. | |
| 2008/0082162 A1* | 4/2008 | Boismier et al. | 623/1.38 |
| 2008/0097571 A1 | 4/2008 | Denison et al. | |
| 2008/0097580 A1 | 4/2008 | Dave | |
| 2008/0103584 A1 | 5/2008 | Su et al. | |
| 2008/0147165 A1 | 6/2008 | Hossainy et al. | |
| 2008/0177373 A1 | 7/2008 | Huang et al. | |
| 2008/0177374 A1 | 7/2008 | Zheng et al. | |
| 2008/0243243 A1 | 10/2008 | Williams et al. | |
| 2009/0030507 A1* | 1/2009 | Klocke et al. | 623/1.46 |
| 2009/0095715 A1 | 4/2009 | Sabaria | |
| 2009/0096137 A1 | 4/2009 | Williams et al. | |
| 2009/0099639 A1 | 4/2009 | Sabaria | |
| 2009/0105800 A1 | 4/2009 | Sabaria | |
| 2009/0146348 A1 | 6/2009 | Huang et al. | |
| 2009/0208555 A1 | 8/2009 | Kuttler et al. | |
| 2009/0216309 A1 | 8/2009 | Granada et al. | |
| 2009/0228094 A1 | 9/2009 | Yan et al. | |
| 2010/0049300 A1* | 2/2010 | Harder | 623/1.15 |
| 2010/0198331 A1 | 8/2010 | Rapoza et al. | |
| 2010/0217370 A1* | 8/2010 | Scheuermann et al. | 623/1.11 |
| 2010/0244329 A1* | 9/2010 | Hossainy et al. | 264/479 |
| 2010/0292773 A1 | 11/2010 | Schmid et al. | |
| 2011/0022163 A1 | 1/2011 | Wang et al. | |
| 2011/0054591 A1 | 3/2011 | Sahatjian et al. | |
| 2011/0160757 A1 | 6/2011 | Ferrera et al. | |
| 2011/0238158 A1 | 9/2011 | Heringes et al. | |
| 2012/0071962 A1 | 3/2012 | Huang et al. | |
| 2012/0187606 A1 | 7/2012 | Zheng et al. | |
| 2012/0226345 A1 | 9/2012 | Zheng et al. | |
| 2012/0271396 A1 | 10/2012 | Zheng et al. | |
| 2013/0084322 A1 | 4/2013 | Wu | |
| 2013/0150943 A1 | 6/2013 | Zheng et al. | |
| 2013/0190676 A1 | 7/2013 | Dickinson et al. | |

(56) References Cited

U.S. PATENT DOCUMENTS

| | | |
|---|---|---|
| 2013/0331927 A1 | 12/2013 | Zheng et al. |
| 2014/0128959 A1* | 5/2014 | Gale et al. .................. 623/1.15 |
| 2014/0188243 A1 | 7/2014 | Zheng et al. |
| 2014/0350659 A1 | 11/2014 | Zheng et al. |
| 2015/0025619 A1 | 1/2015 | Zheng et al. |

FOREIGN PATENT DOCUMENTS

| | | |
|---|---|---|
| JP | H11512626 A | 11/1999 |
| JP | 2000202032 A | 7/2000 |
| JP | 2003500101 A | 1/2003 |
| JP | 2004149692 A | 5/2004 |
| JP | 2005298617 A | 10/2005 |
| JP | 2006192111 A | 7/2006 |
| JP | 2006223860 A | 8/2006 |
| WO | WO-9204393 A1 | 3/1992 |
| WO | WO-0195834 A1 | 12/2001 |
| WO | WO-03034940 A2 | 5/2003 |
| WO | WO-2004052420 A2 | 6/2004 |
| WO | WO-2004080332 A2 | 9/2004 |
| WO | WO-2004110315 A1 | 12/2004 |
| WO | WO-2004110515 A1 | 12/2004 |
| WO | WO-2004080332 A3 | 4/2005 |
| WO | WO-2005096992 A1 | 10/2005 |
| WO | WO-2005115277 A2 | 12/2005 |
| WO | WO-2005115277 A3 | 5/2007 |
| WO | WO-2007126599 A2 | 11/2007 |
| WO | WO-2007146354 A2 | 12/2007 |
| WO | WO-2008002479 A2 | 1/2008 |
| WO | WO-2008002636 A2 | 1/2008 |
| WO | WO-2008005390 A1 | 1/2008 |
| WO | WO-2008008416 A1 | 1/2008 |
| WO | WO-2008011048 A2 | 1/2008 |
| WO | WO-2007146354 A3 | 2/2008 |
| WO | WO-2008016667 A2 | 2/2008 |
| WO | WO-2008016696 A2 | 2/2008 |
| WO | WO-2008016696 A3 | 3/2008 |
| WO | WO-2008033263 A2 | 3/2008 |
| WO | WO-2008002636 A3 | 4/2008 |
| WO | WO-2008051867 A2 | 5/2008 |
| WO | WO-2007126599 A3 | 7/2008 |
| WO | WO-2008089434 A2 | 7/2008 |
| WO | WO-2008051867 A3 | 8/2008 |
| WO | WO-2008002479 A3 | 9/2008 |
| WO | WO-2008016667 A3 | 11/2008 |
| WO | WO-2008137821 A1 | 11/2008 |
| WO | WO-2008011048 A3 | 3/2009 |
| WO | WO-2008033263 A3 | 4/2009 |
| WO | WO-2014091438 A2 | 6/2014 |

OTHER PUBLICATIONS

Breiby, et al. Quantification of preferential orientation in conjugated polymers using X-ray diffraction. J. Polymer Science Part B: Polymer Physics. 2003; 41(20):2375-2393.

Cruz, et al. Quantitative mapping of the orientation of fibroin beta-sheets in B. mori cocoon fibers by scanning transmission X-ray microscopy. Biomacromolecules. Mar. 2006;7(3):836-43.

Donald, et al. Electron Microscopy of Banded Structures in Oriented Thermotropic Polymers. J. Materials Science. 1983; 18:1143-1150.

Fuhrman, et al. Central nervous system. From 'Tissue Engineering: From Lab to Clinic' edited by Pallua et al. 2010; Ch12:221-244.

Hacker, et al. Synthetic polymers. From 'Principles of Regenerative Medicine 2nd ed.' Edited by Atala et al. 2011; Ch 33:587-622.

Hara. Ion-containing polymers and their biological interactions. Polyelectrolytes Science and Technology. 1993; Ch 6:321-325.

Hombreiro-Perez, et al. Non-degradable microparticles containing a hydrophilic and/or a lipophilic drug: preparation, characterization and drug release modeling. J Control Release. Mar. 26, 2003;88(3):413-28.

Lamberti, et al. Real-time orientation and crystallinity measurements during the isotactic polypropylene film-casting process. J. Polymer Science Part B: Polymer Physics. 2003; 41(9):998-1008.

Lee, et al. Retardation of enzymatic degradation of microbial polyesters using surface chemistry: effect of addition of non-degradable polymers. Surface Science. 2003; 542(3)235-243.

Ma, et al. Scaffolding in Tissue Engineering. 2005; pp. 78-80.

Majoros, et al. Poly(amidoamine) dendrimer synthesis and characterization. Dendrimer-based Nanomedicine. 2008; Ch 3:35-57.

Qin, et al. Synthesis and Characterization of Unsaturated Thermotropic Polyesters Prepared via Acyclic Diene Metathesis Polymerization. Macromolecules. 2004; 37:5239-5249.

Sanders. Controlled delivery systems for peptides. From 'Peptide and protein drug delivery' Edited by Vincent Lee, Advances in Parenteral science vol. 4. 1990; Ch 19:785-806.

Seal, et al. Polymeric biomaterials for tissue and organ regeneration. Materials Science and Engineering. R34. 2001; 147-230.

Shastri. Non-degradable biocompatible polymers in medicine: past, present, and future. Current Pharmaceutical Biotechnology. 2003; 4:331-337.

Tanimoto, et al. Comparison of in vivo acute stent recoil between the bioabsorbable everolimus-eluting coronary stent and the everolimus-eluting cobalt chromium coronary stent: insights from the ABSORB and SPIRIT trials. Catheter Cardiovasc Interv. Oct. 1, 2007;70(4):515-23.

Valimaa, et al. Viscoelastic memory and self-expansion of self-reinforced bioabsorbable stents. Biomaterials. Sep. 2002;23(17):3575-82.

Weir, et al. Processing, Annealing and Sterilisation of Poly-L-Lactide. Biomaterials. 2004; 25:3939-3949.

\* cited by examiner

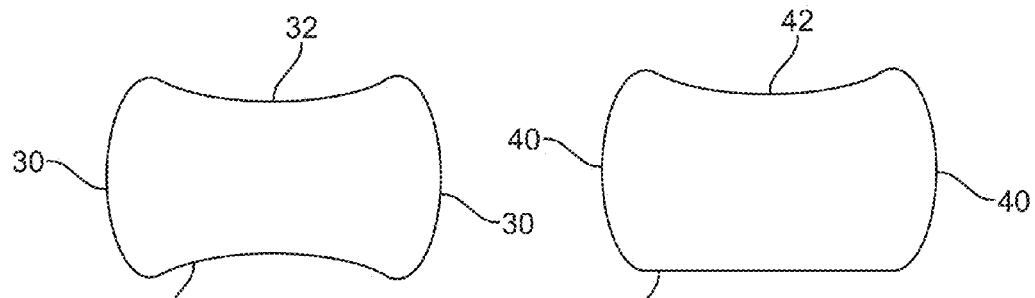
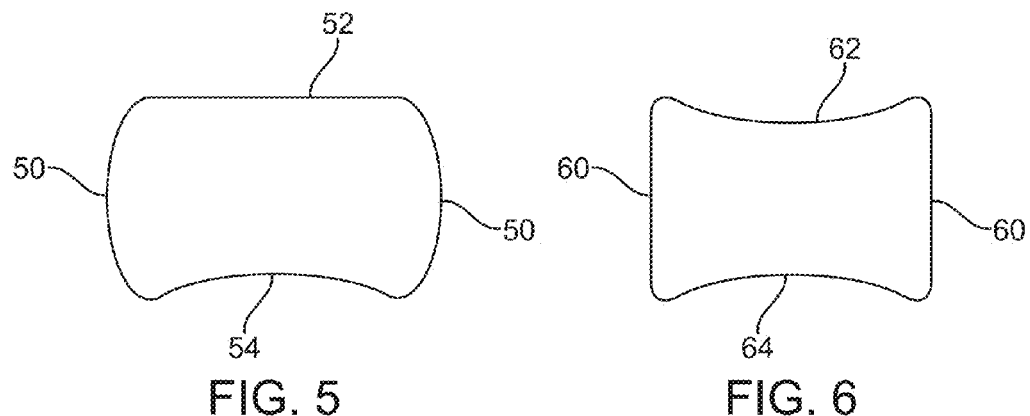
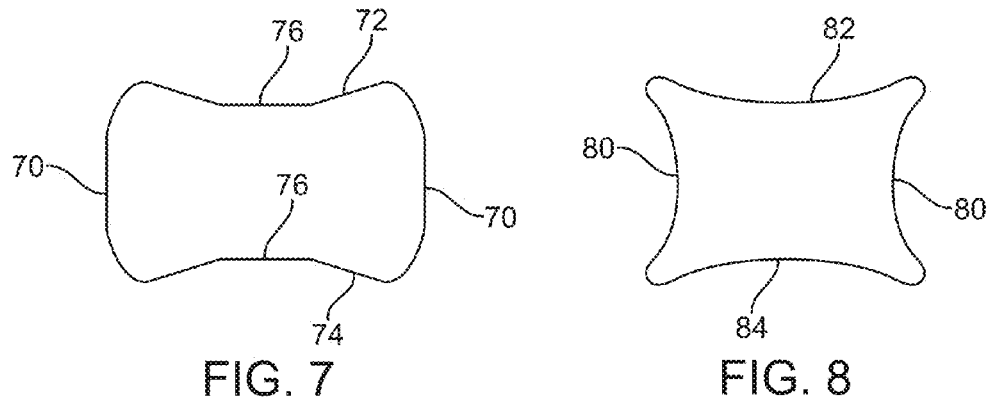
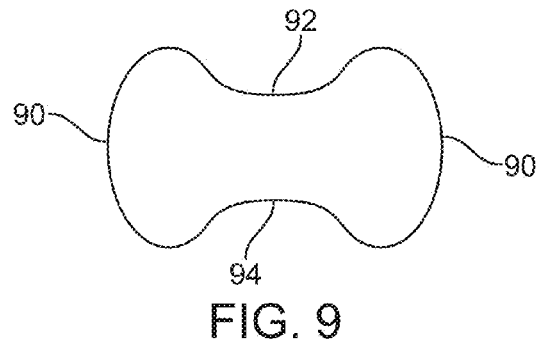

BIODEGRADABLE ENDOPROSTHESES AND METHODS OF THEIR FABRICATION

CROSS-REFERENCE

This application is a continuation-in-part of U.S. patent application Ser. No. 14/461,159, filed Aug. 15, 2014, which is incorporated herein by reference.

FIELD OF THE INVENTION

The present invention relates generally to medical devices and methods for their fabrication. In particular, the present invention relates to the fabrication of biodegradable endoprostheses, such as stents, having shaped surfaces for enhanced implantation performance, enhanced drug delivery or other enhanced properties.

Stents are generally tubular-shaped devices which function to hold open or reinforce a segment of a blood vessel or body lumen, such as a coronary artery, carotid artery, saphenous vein graft, or femoral artery. They also are suitable to support and hold back a dissected arterial lining that could otherwise occlude the body lumen, to stabilize plaque, or to support/hold open a bioprosthetic valves. Stents can be formed from various materials, particularly polymeric and/or metallic materials, and may be non-degradable or biodegradable. Stents are typically delivered to the target area within the body lumen using a catheter. With balloon-expandable stents, the stent is mounted onto a balloon catheter, navigated to the appropriate area, and the stent is expanded by inflating the balloon. A self-expanding stent is delivered to the target area and released, expanding to treat the disease.

Of particular interest to the present invention are biodegradable stents, including polymer stents, such as biodegradable polymer stents or also called scaffolds and other endoprostheses. Biodegradable scaffolds are usually formed from polymers which degrade by various mechanisms such as by hydrolysis and other reaction mechanisms in the vascular or other body environment. This invention also applies to metallic biodegradable stents.

Biodegradable polymer implantable devices and methods of making them are also described in commonly owned U.S. Pat. Nos. 8,182,890; 8,323,760; 8,636,792; 8,814,930; and U.S. Patent Publication Nos. 2008/0177373 and 2006/0029711 the entire disclosure of each of which is incorporated herein by reference.

SUMMARY OF THE INVENTION

In one embodiment, an expandable biodegradable stent prosthesis includes a tubular expandable stent prosthesis body formed from a biodegradable polymeric material, said expandable stent prosthesis body comprising struts and crowns having luminal and abluminal surfaces; wherein at least some of the body abluminal surfaces are concave across substantially the width of said body surfaces; and wherein said stent prosthesis is expandable from a crimped configuration to an expanded larger configuration to support a blood vessel. In one embodiment, the expandable stent prosthesis body comprises struts and crowns each having abluminal surface and luminal surface. In another embodiment, the expandable stent prosthesis body comprises struts, crowns, and links, each having abluminal surface and luminal surface. In a preferred embodiment each strut, crown, and link, each have abluminal surface, luminal surface, and two side surfaces.

In another embodiment, the expandable stent prosthesis body comprises expandable serpentine rings, each ring is composed of struts joined by crowns, and each ring is connected to an adjacent ring by at least one link.

In a further embodiment, the struts and crowns have two side surfaces extending between the luminal and abluminal surfaces, wherein at least some of the side surfaces are convex.

In an additional embodiment, the expandable prosthesis is formed of a biodegradable polymeric material which comprises at least two biodegradable polymers.

In another embodiment, the expandable prosthesis body has been treated to form the concave abluminal surfaces.

In a further embodiment, the expandable stent prosthesis body has been patterned from a tube by a laser.

In another embodiment, the expandable stent prosthesis body has been patterned from a tube by a laser and wherein the struts and crowns have been treated to form the concave abluminal surfaces and convex side surfaces.

In one embodiment, the treatment includes shaping by application of a solvent by at least one of dipping, spraying, or contact with a solvent vapor. In another embodiment, the treatment includes shaping by tumbling, agitating, deburring, scraping, media blasting, laser treatment or heat treatment.

In another embodiment, a coating of at least one drug is formed over at least some portions of the expandable stent prosthesis body.

In a further embodiment, the stent prosthesis further comprises a coating over the expandable stent prosthesis body and said abluminal surfaces of said struts and crowns remaining substantially concave and said side surfaces of said struts and crowns remaining substantially convex.

In one embodiment, a weight of the expandable stent prosthesis after treatment is substantially the same as before treatment.

In one embodiment, the biodegradable polymeric material has an elastic modulus of at least 0.35 GPa.

In another embodiment, the biodegradable polymeric material comprises one or more of polymers and copolymers.

In one embodiment, the prosthesis is capable of being expanded from a crimped diameter to a deployed diameter at body temperature without fracture.

In another embodiment, the prosthesis is capable of being expanded from a crimped diameter to a deployed diameter at body temperature without substantial rotation of at least one of the struts, crowns or links about their axis.

In one embodiment, the biodegradable polymeric material comprises at least one material selected from the group consisting of lactides, poly-DL-Lactide, polylactide-co-gycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

In a further embodiment, the prosthesis is balloon expandable.

In one embodiment, the treatment does not significantly dissolve the polymeric material from which said prosthesis is formed.

In another embodiment, said prosthesis has been treated to shift material from the surface of some struts and/or crowns to an immediately adjacent surface of a strut or crown without a substantial change in body weight of said expandable stent prosthesis.

In another embodiment, the biodegradable polymeric material has a molecular weight from 100 KDa to 1000 Kda.

In a further embodiment, said body has been treated to adjust a thickness of the plurality of struts and crowns from a first thickness before treatment to a second thickness after treatment, wherein the second thickness is greater than the first thickness.

In one embodiment, the treatment causes a thickness of a plurality of struts and crowns between the luminal and abluminal surfaces to increase while a width of the struts and crowns between the side surfaces remains substantially the same.

In another embodiment, the treatment comprises exposing the expandable prosthesis to a solvent for a predetermined period of time provide at least some substantially convex side surfaces and at least some concave abluminal surfaces of said struts and crowns.

In another embodiment, the treatment causes a thickness of the plurality of struts and crowns between the luminal and abluminal surfaces to increase while decreasing a minimum width of the struts and crowns between the side surfaces by redistributing the polymeric material.

In one embodiment, a stent prosthesis comprises a tubular expandable stent prosthesis body formed from a biodegradable polymeric material, said polymeric material is patterned into a stent radially expandable from a crimped diameter to a deployed larger configuration, wherein the stent comprises a plurality of struts joined by crowns, wherein said struts and crowns each have a luminal surface, an abluminal surface, and two side surfaces extending between the luminal and abluminal surfaces; and wherein at least some of the side surfaces have a convex shape across substantially the thickness of said side surfaces; said stent prosthesis in the deployed diameter has sufficient strength to support a blood vessel. In another embodiment, the stent comprises a plurality of struts joined by crowns, wherein at least some of the crowns are connected to adjacent crowns by a link. In another embodiment, the stent comprises a plurality of struts joined by crowns, wherein at least some of the crowns are connected to adjacent crowns.

In another embodiment, at least some of the struts and crowns abluminal surfaces have a concave shape across substantially the width of said struts and crowns abluminal surfaces.

In a further embodiment, substantially all of the side surfaces have a convex shape across substantially the thickness of said side surfaces.

In one embodiment, said prosthesis has been treated by contact with a solvent to redistribute said polymeric material to provide said concave and convex surfaces.

In one embodiment, said prosthesis has been treated by contact with a solvent to flow said polymeric material to provide said concave and convex surfaces.

In a metal or metal alloy degradable stent, such as zinc, magnesium, and iron, and alloys thereof, wherein the stent is treated to modify at least some abluminal surfaces making them concave substantially across the width of said abluminal surfaces, and/or modifying at least some of side surfaces making them substantially convex across the thickness of said side surfaces. In another embodiment, the above surface modifications are provided without a substantial change in weight compared to before treatment, or without losing more than 15% in weight after treatment, or without substantially losing more than 25% in weight after treatment.

In another embodiment, said prosthesis has been treated by contact with a solvent to redistribute said polymeric material to provide an increased thickness of said side surfaces and decreased width of said abluminal and luminal surfaces.

It can be appreciated that embodiments can be combined together in whole or parts throughout this document.

BRIEF DESCRIPTION OF THE DRAWINGS

FIG. 3 is a cross section of a stent structure having a concave abluminal surface, a concave luminal surface, and two convex side surfaces;

FIG. 4 is a cross section of a stent structure having convex side surfaces, a concave abluminal surface and a substantially straight/flat luminal surface;

FIG. 5 is a cross section of a stent structure having two convex side surfaces, a substantially straight/flat abluminal surface and a concave luminal surface;

FIG. 6 is a cross section of a stent structure having substantially straight side surfaces, a concave abluminal surface and a concave luminal surface;

FIG. 7 is a cross section of a stent structure having convex side surfaces, a concave abluminal surface and a concave luminal surface with straight substantially center portions;

FIG. 8 is a cross section of a stent structure having concave side surfaces, a concave abluminal surface and a concave luminal surface;

FIG. 9 is a cross section of a stent structure having a dogbone shape comprising concave luminal and abluminal surfaces, and convex side surfaces;

DETAILED DESCRIPTION OF THE INVENTION

Laser patterning or cutting of stents or scaffolds from a tube or sheet of polymeric material provides struts or other stent structures, with many having substantially rectangular or square cross sections. Each strut or other structure of the scaffold cross sections according to the present invention provide certain surface geometry or are modified according to the treatment processes described herein to provide certain geometry.

Figure 1:
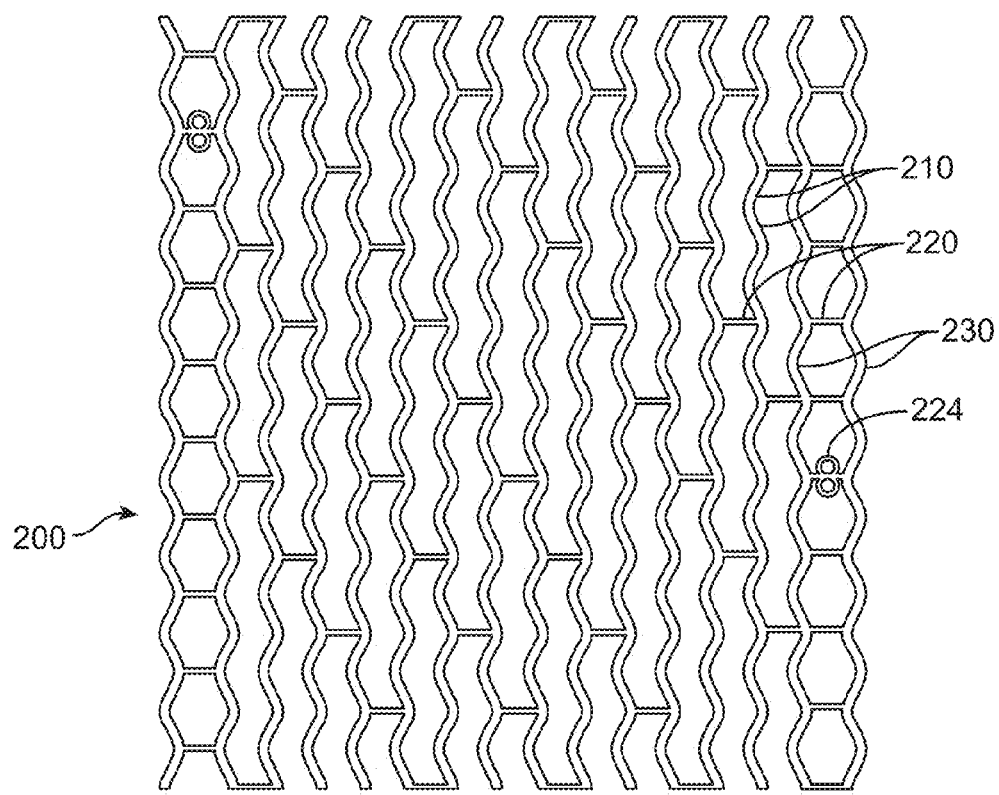
FIG. 1 depicts an example of a two dimensional stent pattern, a two dimensional stent structure, or a two dimensional stent body.

An exemplary scaffold pattern is shown in FIG. 1 represented in two dimensions. The scaffold, scaffold structure, or scaffold body 200 has sinusoidal rings comprising struts 210 which are joined by V or U shaped crowns 230. The rings are interconnected by links 220. In the example scaffold pattern shown, links 220 connect adjacent crowns. A length of the scaffold can be adjusted by changing a number of rings. Some of the links 220 or struts 210 may be replaced by or attached to one or more loops 224 each containing one, two or more radiopaque markers axially or radially or somewhere in between. For example two such pairs of radiopaque markers can be provided at the opposite ends of the scaffold, and/or at the opposite side of the scaffold. The scaffold 200 can be balloon expandable and has low recoil, sufficient radial strength to support a body lumen, conformable to the body lumen, and has low percent shortening upon expansion of less than 15%. Many other scaffold structures include differing arrangements of struts, crowns, links and other structures which together form a balloon expandable stent, stent structure, or stent body, and can be modified according to the methods described herein. The scaffold can also be self expandable, or self expands prior to balloon expansion, or can self expand to a second larger diameter than a first deployed diameter after recoil from said first deployed diameter. The scaffold structures (e.g. struts) have luminal and abluminal surfaces and two side surfaces extending between the luminal and abluminal surface as can be seen in the cross sectional views of FIGS. 2-9. Struts in this example have a thickness of 100 micron, strut thickness can range from 25 micron to 300 micron, preferably 75 micron to 200 micron, or other, strut length in this example have a length of 0.75 mm, strut length can range from 0.35 mm to 3 mm, preferably from 0.5 mm to 1.5 mm, or other. Struts width in this example are 150 micron, can range from 50 to 200 micron, or other.

Other embodiments of scaffolds and materials and treatments therefore are described in further detail in U.S. Pat. Nos. 8,182,890; 8,323,760; 8,636,792; 8,814,930; and U.S. Patent Publication Nos. 2008/0177373 and 2006/0029711 which have been previously incorporated by reference herein.

Figure 17:
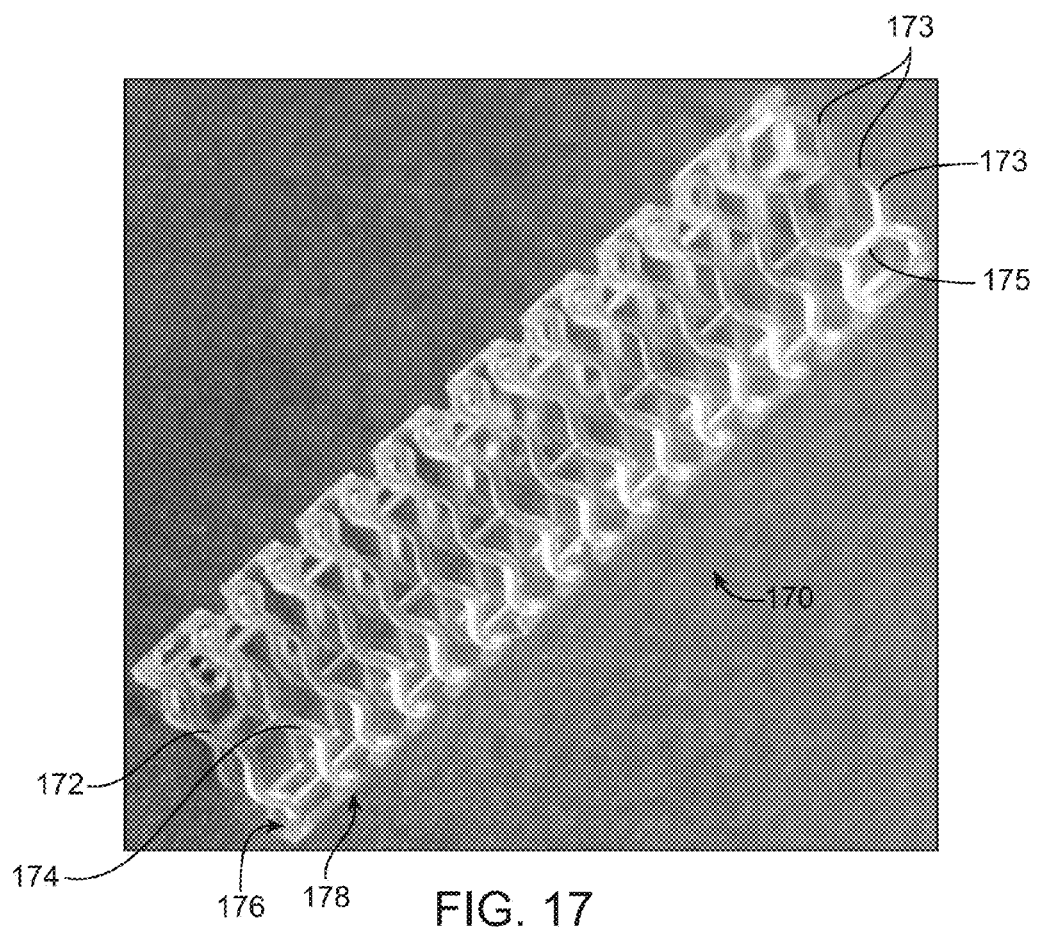
FIG. 17 is a perspective view of one example of a stent, stent structure, or stent body, showing the stent pattern.

An alternative exemplary patterned stent 170 is shown in FIG. 17. The patterned stent, stent, stent body, or stent structure 170 has struts 174 joined by crowns 172. The patterned stent has luminal surfaces 176 facing the lumen of the blood vessel, and abluminal surfaces 178 which faces the blood vessel wall or faces the lumen wall. Each of the scaffold structures such as struts, crowns, and links, has two side surfaces extending between the luminal and abluminal surfaces. The rings 173 each comprise struts 174 joined by crowns 172. The ring 173 can be in-phase or out-of-phase or a combination thereof and are interconnected by links 175. The rings 173 are connected to an adjacent ring by links 175, or also some adjacent crowns are connected by links 175. Some of the links 175 may be attached to or replaced by one or more loops each containing one, two or more axially or radially displaced radiopaque markers or radiopaque markers may be placed in the end rings of the patterned stent. The patterned stent 170 is balloon expandable and has low recoil, sufficient radial strength to support a body lumen or blood vessel, conformability to the body lumen or blood vessel, and low percent shortening upon expansion of less than 15%.

Many other stent patterns include differing arrangements of struts, crowns, links and other structures which together form a balloon expandable structure. Two such examples are shown in FIGS. 18 and 19.

Figure 18:
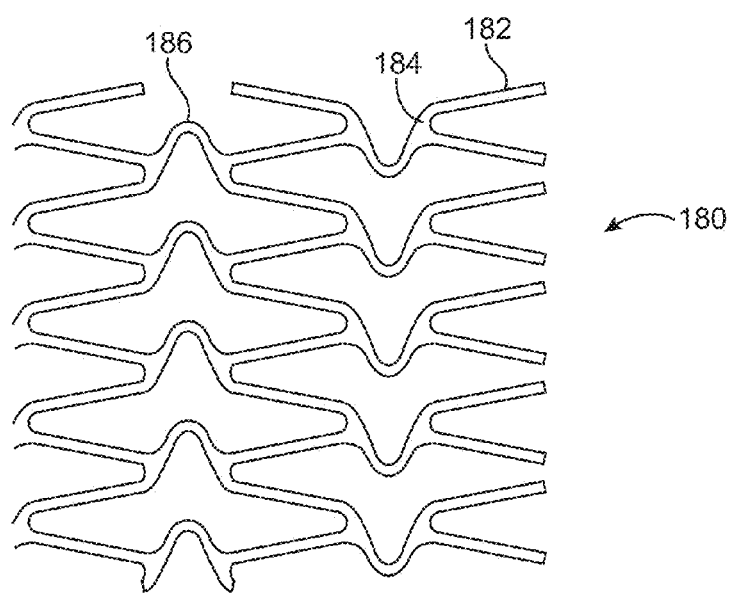
FIG. 18 is a two dimensional top view of another example of a part of a stent, stent structure, or stent body, showing the stent pattern.

FIG. 18 depicts a two dimensional view of a part/portion of a patterned stent 180 having a plurality of struts 182 joined by crowns 184. As shown in FIG. 18, the crowns 184 are connected by U-shaped links 186 which alternate in directions (upward and downward directed) depending on axial location along the length of the stent. The U-shaped links 186 may be replaced with straight, S-shaped, W-shaped or other shaped links and may be positioned at every crown or at some crowns, every other crown, or other numbers of crowns. In addition to links connecting adjacent rings, typically connecting adjacent crowns of adjacent rings, links can also connect/interconnect struts to other struts or crowns of adjacent rings. In addition to or as an alternative to rings, or serpentine ring patterns, helically wound rings, or helically wound serpentine patterns can also be used.

Figure 19:
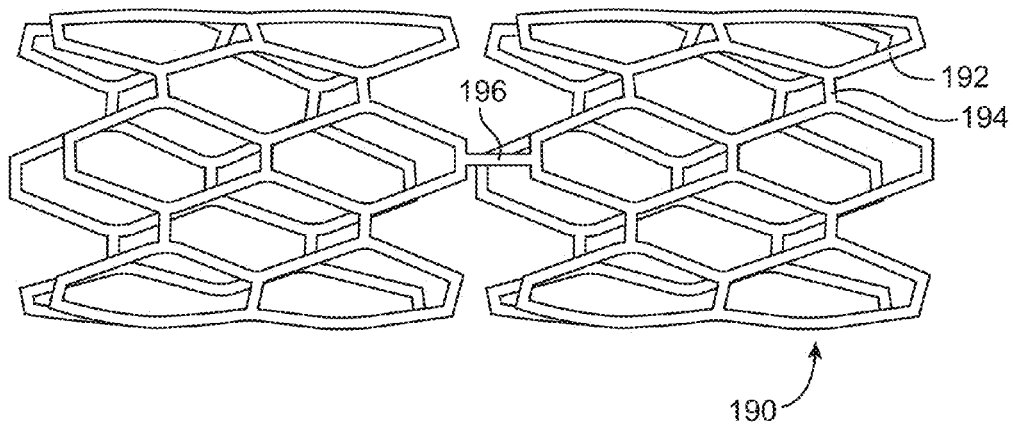
FIG. 19 is a side perspective view of another example of a stent, stent structure, stent body, showing the pattern.

FIG. 19 depicts another example of a patterned stent 190 having struts 192 and crowns 194 joining struts. Optionally as seen in the patterned stent of FIG. 19, link 196 connects two adjacent crowns. The links 196 may be straight, sinusoidal, or other shaped. One, two or more links 196 can connect the stent rings. The struts shown in the stent examples of FIGS. 1 and 17-19 are straight, however some or all of these straight struts can be replaced by curved or other shaped struts. Struts can be axially aligned in a crimped configuration or can be at an angle to the longitudinal axis. Upon expansion of the stent, generally the angle between the struts and the longitudinal axis of the stent increases.

In a stent pattern, generally crowns join struts, in one embodiment crowns join two struts, in other embodiment crowns join three or four struts, or other. Crowns can be straight, arc, semi-circular, or key hole shaped, or other crown shapes that connect struts. Struts can be straight, wavy, or other strut shapes. In some embodiments struts extend axially, in another embodiment struts extend in a helical direction, or other direction such as between an axial direction and a radial direction. Crowns can be connected to adjacent crowns. In one embodiment, crowns are connected to adjacent crowns by a link, such link can be straight links, or have other shapes such as U, V, W, S, or other shapes or geometries. Crowns connected to adjacent crowns by links typically connected on any points or areas along the length of the crown. In another embodiment, crowns are connected to adjacent crowns without a link, at the point of intersection of the adjacent crowns or at any other point along the length of the adjacent crowns where they meet. In another embodiment, crowns are connected to adjacent crowns by fusing the two crowns into one, such as in the embodiment of FIG. 19.

The term "stent" or "scaffold structures" or "stent structures" or "stent elements" or "stent body" as used herein comprise struts, links, crowns, elements or other structural components of the stent prosthesis. Together these structural components form a stent, scaffold, stent body, prosthesis body, body, or stent structure.

The substantially flat (flat sheet) or slightly convex (tubular body) abluminal surface and substantially flat/straight side surfaces of the scaffold structures created during laser cutting are modified to provide a shape which improves mechanical performance of the scaffold and/or provides improved drug delivery from the scaffold or from a coating on the shaped scaffold. The polymeric tubular body is usually formed as a substantially continuous cylinder free from holes or other discontinuities. The modified surfaces formed by the methods described herein occur on some or substantially all parts of the scaffold structure comprising the struts, crowns, links and/or other scaffold structures.

In one embodiment, the substantially flat side surfaces of the scaffold struts, crowns, links and/or other structures extending between the luminal and abluminal surfaces of the scaffold created by a fabrication process such as laser cutting can be modified to form substantially convex side surfaces, preferably convex side surfaces substantially along the thickness of the structure. The convex side surfaces function to more widely distribute tensile stresses and compressive stresses along the scaffold and can increase radial strength of the scaffold. The dimension of the scaffold structure between the luminal and abluminal surfaces is the thickness of the scaffold structures or stent. The convex curvature/shape of the side surfaces extends substantially across the thickness of the surfaces such as the thickness of the strut, crown, or link.

In another embodiment, the substantially flat or slightly convex abluminal surfaces of the scaffold struts, crowns, or links and/or other structures can be modified by the processes/treatment described herein to form substantially concave abluminal surfaces. In another embodiment, the substantially flat or slightly concave luminal surfaces of the scaffold struts, crowns, or links and/or other structures can be modified by the processes/treatment described herein to form substantially concave luminal surfaces. The resulting concave abluminal surfaces can provide benefits in drug coating and in drug delivery and benefits of embedding the scaffold into the vessel wall and the convex side surfaces can provide benefits in retaining the scaffold on a balloon catheter, and also improved trackability in tortuous anatomy. The dimension of the scaffold structure between the side surfaces is the width of the scaffold structure. The concave curvature of the abluminal and/or luminal surfaces extends substantially across the width of these surfaces. In a preferred embodiment, the stent prosthesis is further coated with a coating comprising at least one drug and at least one polymer, wherein the coating contours to the concave abluminal surfaces and convex side surface conforming to such shapes, in a preferred embodiment, without substantially changing the luminal, abluminal or side surface shapes.

In another embodiment, the substantially flat luminal and abluminal surfaces of the scaffold struts, crowns, links and other structures can be modified by the processes described herein to form substantially dumbbell, barbell, bow tie, or dogbone shaped cross sections.

Figure 2:
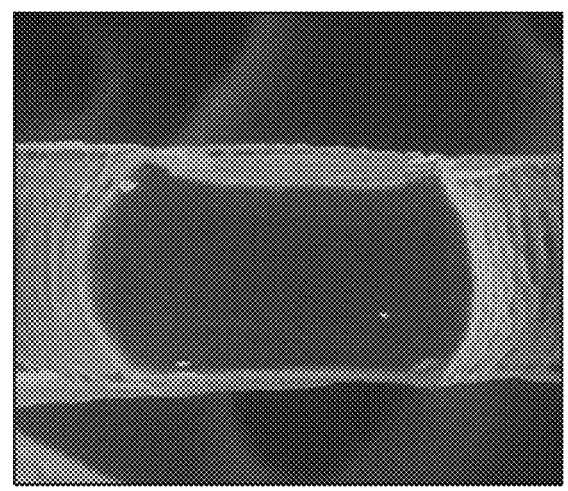
FIG. 2 is an SEM image showing a cross section of a stent structure, a stent strut in this image.

FIG. 2 is an SEM image showing a cross section of a scaffold strut of one embodiment which has been modified to have a shape designed for improved scaffold performance. The stent of FIG. 2 has a luminal surface (bottom), an abluminal surface (top), and two side surfaces. As shown in FIG. 2, the abluminal surface is substantially concave across the width of the abluminal surface while the two side surfaces are substantially convex across the thickness of the side surfaces of the strut. This fabricated shape or modified/treated shape can distribute tensile stresses and compressive stresses along of the scaffold and can provide improved radial strength of the scaffold. The SEM image of FIG. 2 is taken at a magnification of 1200× to show the scaffold structure features in the micron level.

Figure 20:
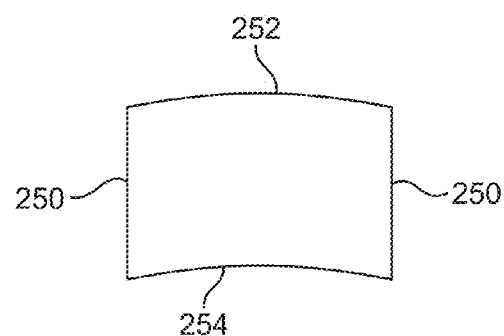
FIG. 20 is an example of a tubular stent strut cross section before treatment.

FIG. 20 shows an example of a cross section of a scaffold strut or other scaffold structure before modification or treatment when the strut is a part of a stent formed from a tube. The abluminal surface 252 of the untreated strut is slightly convex due to the overall curvature of the tube. Similarly, the luminal surface 254 is slightly concave due to the curvature of the tube. The side surfaces 250 extend from the abluminal to the luminal surfaces and may be parallel or non-parallel depending on the process used to form the tubular stent but are generally flat/straight.

In one embodiment, the modification of the scaffold surface shapes improves tracking and/or push by reducing the force required to track or push the scaffold mounted on a catheter through a cylindrical body, such as a blood vessel. The reduction of track or push force is achieved by changing the area of surface contact between the modified scaffold shape and the vessel. On the abluminal side, the unmodified surfaces on the scaffold structure can act like ratchet elements as the scaffold is pushed through a blood vessel, especially one with calcified lesions. This may hinder tracking through the vessel because the unmodified sides can get caught on the walls of the vessel. On the luminal side, the unmodified sides of the scaffold can inhibit a guidewire or catheter from going through one of the spaces between scaffold structures, such as for treatment of a bifurcation. In order to improve tracking or passage of guidewire and catheter, it is beneficial to modify the shapes of the surfaces on the scaffold structure. The modification of the shape of the surfaces to provide convex surfaces, concave surfaces or a combination thereof improves performance of the scaffold.

Examples of processes which can be used to shape the surfaces of the scaffold structures include solvent treatment, media blasting, abrasive tumbling, mechanical shaping, laser shaping, heat treatment or other shaping processes. The processes of shaping the surfaces of the scaffold create substantially convex side surfaces extending from the luminal to the abluminal edge. In one embodiment, the convex side surfaces can have radii of curvatures of about 0.020 to about 0.375 mm, about 0.030 to about 0.200 mm, or about 0.050 to about 0.175 mm. The processes of shaping the surfaces of the scaffold can also create substantially concave abluminal surfaces extending between the side surfaces. In another embodiment, the concave luminal and/or abluminal surfaces can have radii of curvatures of about 0.020 to about 0.500 mm, about 0.030 to about 0.200 mm, or about 0.050 to about 0.175 mm. The concavity of the abluminal surfaces extends substantially across the width from one side surface of the scaffold structure to the other side surface of the same structure, with a single concave depression, or a concave shape. Similarly, the convex side surfaces of the scaffold structures extend across the thickness substantially from the luminal to the abluminal surface as one convex surface, or as a convex shape.

The scaffold structures can be shaped before and/or after the application of a polymer/drug coating layer to the exterior of the scaffolding. In one embodiment, the shape treatment is performed on the scaffold structure followed by coating with drug matrix coating wherein the coating process does not substantially change the shape of the surfaces but conforms to the concave and convex shapes of the treated surfaces.

In one embodiment, the concave luminal surfaces after the treatment process have a concave shape with a radius of curvature different than the radius of curvature of the inner diameter of the tube from which the scaffold is formed.

In one embodiment, the ratio of radius of curvature of at least a portion of the luminal or abluminal surface of the scaffold structure to the radius of curvature of the side of the scaffold structure is less than one.

In another embodiment, the ratio of radius of curvature of at least a portion of the luminal or abluminal surface of the scaffold structure to the radius of curvature of the side of the scaffold structure is greater than one.

In another embodiment, the radius of curvature of at least a portion of the luminal or abluminal surface of the scaffold structure is substantially equal to the radius of curvature of the side of the scaffold structure.

In one embodiment, the radius of curvature of at least a portion of the concave luminal or abluminal surfaces is greater than the radius of curvature of at least a portion of the convex side surfaces.

In one embodiment, the cross section of the scaffold structure forms a substantially dumbbell, barbell, bow tie, or dogbone shaped cross section structure.

Examples of shaped cross sections of scaffold structures are shown in FIGS. 3-9. These scaffold structures can represent any scaffold structures including struts, crowns or/and links. In one embodiment, the scaffold structure cross section of FIG. 3 includes a concave abluminal surface 32 and a concave luminal surface 34 and two convex side surfaces 30 extending between the luminal and abluminal surfaces of the scaffold structure. The convex shape of the side surfaces 30 extends substantially across the thickness of the scaffold structure. The concave shape of the abluminal and luminal surfaces 34, 32 extends substantially across the width of the scaffold structure surface.

In another embodiment, the strut cross section of FIG. 4 includes two convex side surfaces 40, as well as a concave abluminal surface 42 and a substantially flat luminal surface 44. The strut cross section of FIG. 5 includes two convex side surfaces 50, as well as a substantially flat abluminal surface 52 and a concave luminal surface 54. The strut cross section of FIG. 6 includes substantially flat side surfaces 60, as well as a concave abluminal surface 62 and a concave luminal surface 64. The strut cross section of FIG. 7 includes convex side surfaces 70, as well as a concave abluminal surface 72 and a concave luminal surface 74. The concave abluminal and luminal surfaces 72, 74 may include a substantially flat center portion 76 which forms a bottom part of the concave surface. Similarly, the convex side surfaces 70 can include flat portions. The strut cross section of FIG. 8 includes two concave side surfaces 80, as well as a concave abluminal surface 82 and a concave luminal surface 84.

The strut cross section of FIG. 9 includes substantially convex side surfaces 90, as well as a concave abluminal surface 92 and a concave luminal surface 94 and rounded intersection of the concave and convex surfaces, which together form a dogbone shaped cross section. In the example of FIG. 9, the structures can embed or nest the scaffold into the vessel wall upon expansion providing better scaffold apposition to the surrounding tissue. In contrast, square or rectangular flat cross section abluminal strut surfaces on a scaffold may inhibit embedding because the substantially flat surfaces push on the uneven plaque covered vessel wall during expansion.

Although the cross sections of FIGS. 3-9 have been shown as symmetrically shaped about a midline of the struts, the cross sections can also be asymmetrically shaped. In one embodiment, at least a portion of the scaffold structure with a concave abluminal surface will have a minimum cross sectional thickness of between 50 to 300 microns, preferably between 75 to 200 microns, more preferably from 100 to 150 microns.

In one embodiment, at least a portion of the scaffold structure with a concave abluminal surface will have a maximum cross sectional thickness of between 50 to 500 microns, preferably between 75 to 300 microns, more preferably from 100 to 200 microns.

In one embodiment, at least a portion of the scaffold structure with a convex side surface will have a minimum cross sectional width of between 50 to 300 microns, preferably between 75 to 300 microns, more preferably from 100 to 150 microns.

In one embodiment, at least a portion of the scaffold structure with a convex side surface will have a maximum cross sectional width of between 50 to 500 microns, preferably between 75 to 300 microns, more preferably from 100 to 200 microns.

In one embodiment, after the shaping process treatment, the variance in scaffold structure dimensions along the length of the scaffold is less than 40%, preferably less than 25%, more preferably less than 10%.

In some embodiments, the tubular body, stent or scaffold may be formed from at least one biodegradable polymer or other biodegradable material having desired degradation characteristics where the polymer may be modified to have the desired crystallinity, Tg, recoil, strength, shortening, expansion characteristics, crimping characteristics, molecular weight, and/or other characteristics. Biodegradable polymers include one or more polymers, copolymers, blends, and combination thereof of: lactides, Caprolactones, and Glycolides. Some examples include poly-DL-Lactide, polylactide-co-glycolactide; polylactide-co-polycaprolactone, poly (L-lactide-co-trimethylene carbonate), polylactide-co-caprolactone, polytrimethylene carbonate, elastin, fibrin, collagen and copolymers; polyhydroxybutyrate; polyhydroxyvalerate, poly orthoesters, poly anhydrides, polyiminocarbonates and the like. One embodiment of a biodegradable polylactide based polymer comprises a copolymer of L-lactide and glycolide, preferably with a weight ratio of 85% L-lactide to 15% glycolide. Another embodiment of a biodegradable polylactide based polymer comprises a copolymer of L-lactide and caprolactone, preferably with a weight ratio of 90% L-lactide to 10% caprolactone.

In one example, the tubular body, stent or scaffold comprises a degradable polymeric material wherein the polymeric material comprises one or more polymers; or one or more co-polymers; or one or more blends of monomers, polymers or copolymers; and combinations thereof. In another embodiment, the polymeric material comprises one or more polymer or one or more co-polymer. Additionally, at least one monomer, polymer, or co-polymer of similar material (to the one or more polymer or the one or more co-polymer) is blended with the polymeric material.

In another example, a biodegradable stent comprising a polymeric material comprises a copolymer of lactide and caprolactone in the ratio by weight ranging from 80-99% lactide to 1-20% caprolactone; wherein the polymeric material further comprises a monomer or polymer including a copolymer of one or more of the following: lactide, glycolide, lactide glycolide, caprolactone, and lactide caprolactone; wherein the one or more monomer or polymer total amount is 1 to 100 micrograms per milligram of polymeric material, preferably 5 to 75 micrograms per milligram of polymeric material, more preferably 10 to 50 micrograms per milligrams of polymeric material; wherein the scaffold with the modified structure cross section is capable of being crimped from an expanded configuration to a smaller crimped configuration, and at body temperature capable of being expanded to a deployed configuration, and having sufficient strength when expanded to support a body lumen, without fracture of the stent.

In a further example, the one or more monomer and/or polymer changes (increases or decreases) the crystallinity of the polymeric material by 5% to 150%, preferably by 10% to 75%, more preferably by 10% to 50%. In another example, the one or more monomer and/or polymer controls the crystallinity of the polymeric material to between 1% and 55%, preferably between 1% and 35%. In a further example, the one or more monomer and/or polymer does not change the crystallinity of the polymeric material from being between 1% and 55%. In a further embodiment, the one or more monomer and/or polymer does not substantially change the Tg of the polymeric material. In a further embodiment, the one or more monomer and/or polymer changes (increases or decreases) the Tg temperature of the polymeric material by 1° C. to 15° C., preferably 1° C. to 10° C., more preferably by 1°

C. to 5° C. In yet a further embodiment, the one or more monomer and/or polymer controls the Tg temperature of the polymeric material to between 20° C. and 55° C., preferably to between 35° C. and 50° C., more preferably to between 37° C. and 50° C., most preferably between 37° C. and 45° C.

In other examples, the tubular body, degradable stent or scaffold may comprise at least one non-degradable polymer where the polymer may be modified to have the desired crystallinity, Tg, recoil, strength, shortening, expansion characteristics, crimping characteristics, molecular weight, and/or other characteristics. Non-degradable polymers include for example, a silicone-urethane copolymer, a polyurethane, poly(ethylene), phenoxy, ethylene vinyl acetate, chondroitin sulfatepoly(vinylidene fluoride), poly(vinylidene fluoride-co-hexafluoro propene), poly(tetrafluoroethylene), expanded poly(tetrafluoroethylene), poly(sulfone), polymethylmethacrylate, poly(n-butyl methacrylate), poly(N-vinyl pyrrolidone), copolymers of vinyl monomers and olefins such as poly(ethylene-co-vinyl alcohol) (EVAL), copolymers of acrylonitrile-styrene, ABS resins, and copolymers of ethylene-vinyl acetate, poly(amides) such as Nylon 66 and poly(caprolactam), alkyd resins, poly(oxymethylenes), poly(imides), poly(ester amides), epoxy resins, polyurethanes, rayon, and rayon-triacetate.

In other examples, the tubular body, biodegradable stent or scaffold may comprise at least one degradable or non-degradable biological molecule where the material may be modified to have the desired recoil, strength, shortening, expansion characteristics, crimping characteristics, molecular weight, and/or other characteristics. Biological materials include, for example, albumin, fibrin, fibrinogen, starch, poly(amino acids), peptides, proteins, gelatin, elastin, chondroitin sulfate, dermatan sulfate (a copolymer of D-glucuronic acid or L-iduronic acid and N-acetyl-D-galactosamine), collagen, hyaluronic acid, glycosaminoglycans, polysaccharides, chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

In other examples, the tubular body, biodegradable stent or scaffold may comprise at least one degradable metal where the degradable metal has a desired recoil, strength, shortening, expansion characteristics, crimping characteristics, molecular weight, and/or other characteristics. Degradable materials for the metal stent include can be a suitable metal such as magnesium, zinc, iron, and alloys or combinations thereof. The metal can be modified to exhibit different hardnesses, and thus varying stiffnesses, by well known annealing and manufacturing processes. The tubular body may also comprise combinations of biodegradable polymeric materials and degradable metals.

In one embodiment, the degradable stent prosthesis comprises a metal or metal alloy, optionally formed from a tubular body, wherein the metal or metal alloy comprises zinc, magnesium, and/or iron, or alloys, wherein the stent is treated to modify at least some abluminal surfaces making them concave substantially across the width of said abluminal surfaces, and/or modifying at least some of side surfaces making them substantially convex across the thickness of said side surfaces. In another embodiment, providing the above surface modification without substantially change in weight to before treatment, or without losing more than 15% in weight after treatment, or without substantially losing more than 25% in weight after treatment.

Degradable metal and metal alloys can be treated using the methods described in this application. In addition, treatments using acid such as nitric acid, hydrochloric acid, and/or sulphuric acid can be used to modify the abluminal surfaces to concave, and side surfaces to convex.

1. Structure Shaping by Solvent Treatment

In one embodiment, the scaffold, structure is shaped by exposure to at least one solvent. The exposure to the solvent can be accomplished in a variety of ways such as by dipping, spraying, exposure to solvent vapor or other solvent application processes.

a. Structure Shaping by Solvent Dipping

The scaffold supported lightly on a mandrel is dipped into a first solvent for about 1 second to one minute, 1 second to 30 seconds, or 2 seconds to 10 seconds and is quickly removed. The scaffold can be rinsed in a second solvent to remove materials that are adhering to the scaffold. The solvent and time of exposure is selected based on its ability to move the scaffold material at the side surfaces of the scaffold to the luminal and abluminal surfaces and change the shapes of these surfaces in some embodiments without substantially dissolving the scaffold. In one embodiment, at least a portion of the surfaces on the side, abluminal and luminal surfaces of the struts and other structures can be shaped by inserting a loose mandrel such as a Teflon rod or tube inside the scaffold to support the scaffold during the selected treatment process. Preferably, the outer diameter of the loose mandrel is 0.001" to 0.100" smaller, more preferably 0.005" to 0.015" smaller than the inner diameter of the scaffold for a 2.5 to 4.0 mm scaffold.

In one embodiment, at least some parts of the scaffold structure width change by up to 25%, preferably change by up to 15%, more preferably change by up to 10%. In another embodiment, at least some parts of the scaffold structure thickness change by up to 25%, preferably change by up to 15%, more preferably change by up to 10% as a result of the treatment.

In one embodiment, the scaffold cross section is reduced in width and increased in thickness due to the transfer, flow, or movement of scaffold polymeric material during the solvent shaping process. In one example, the processes of shaping the surfaces of the scaffold can increase the maximum thickness of the scaffold by at least 10%, at least 20%, or at least 30%, when taken in cross section. The maximum width of the struts and other structures can remain the same while the thickness changes as described above or can decrease by at least 10%, at least 20%, or at least 30%, when taken in cross section. The treatment in one embodiment causes the flow of polymeric material from one side surface to an immediately adjacent surface, which may be on the same strut, crown or link In some embodiments, the shaping process can also be due to redistribution of the scaffold material from some surfaces of the scaffold to other surfaces to create the shaped struts with convex side surfaces and concave abluminal surfaces.

In one embodiment, the scaffold mass after shaping process is substantially unchanged from before the treatment process.

In another embodiment, the scaffold mass after the shaping process is decreased by no more than 25%, preferable no more than 10%, more preferably no more than 5%.

The first and second solvent can be a single solvent or a mixture of different solvents. Examples of the first solvent include methylene chloride (DCM), chloroform, tetrahydrofuran, dimethyl-sulfoxide (DMSO), acetone, toluene, xylene, DMF, or the like, or a combination thereof. In one embodiment, the first solvent is any solvent which can dissolve the scaffold if exposed to this solvent for more than 1 minute at room temperature. The second solvent can be any solvent or other fluid which does not measurably dissolve the scaffold if the scaffold is exposed to the second solvent for more than 1 minute at room temperature. In a preferred embodiment, the stent is not dissolved wherein the polymeric material flows from one surface on a stent structure to an adjacent surface on the same stent structure, or one surface on a stent structure to the same surface on the same stent structure.

The first solvent can also be a combination of a solvent that is capable of dissolving the scaffold and a solvent that does not dissolve the scaffold. For example, the first solvent can include a solvent capable of dissolving the scaffold after 1 minute or longer of exposure to the solvent at room temperature and a solvent which does not dissolve the scaffold after 1 minute of exposure at room temperature. One example of such a first solvent combination is 4 parts DCM and 6 parts Ethanol. In one example, the first solvent includes from 0.1 to 10 parts of solvent capable of dissolving the scaffold (such as DCM) and 9.9 parts to 0.1 parts of solvent not capable of dissolving the scaffold (such as Ethanol). The second solvent can be ethanol, methanol, isopropanol, water, aqueous solution, or the like, or combinations therefore.

In one embodiment, the scaffold shaping process utilizes a mixture of solvents to modify the scaffold structure cross section due to the transfer of scaffold material from its width to its thickness.

In one embodiment, the scaffold shaping process utilizes at least one solvent to initiate the modification of the scaffold structure cross section due to the transfer of scaffold material from its width to the thickness and at least another solvent to terminate the process.

Instead of using a second solvent, the scaffold on a mandrel can be shaken or blown with gas to remove excess solvent and/or dried in vacuum, oven, and or pressurized $CO_2$.

Instead of a second solvent, the scaffold can be quickly placed in an oven, vacuum oven, freeze dried or exposed to another known process to remove the first solvent.

Not all of the first or second solvent needs to be removed after the dipping treatment is complete. Additional processes which can be used to remove solvent include heat treatment, exposure to carbon dioxide, freeze drying or vacuum. The scaffold can be transferred to a bigger, tighter mandrel to maintain the dimensions of the scaffold for additional drying such as drying at ambient temperature, elevated temperature, such as below the glass transition temperature of the polymer in an oven, vacuum oven, freeze drying or the like, in a vacuum, or other means.

The scaffold can also be further treated by placing on a tight mandrel and dipping to further shape the abluminal and side surfaces as will be described further below. Additional shaping of the side, abluminal and luminal surfaces of the crowns and axial struts can be achieved by repeating a dipping treatment more than once or by dipping for longer periods of time. Agitating during the dipping treatment can increase the rate of shaping. Spinning or rotating of the scaffold in the solvent can help achieve a more consistent application of the solvent along the length of the scaffold and particularly in tight spaces of the scaffold. Spinning can also change the distribution of the material during shaping, for example to provide a strut shape with a wider abluminal side due to forces on the outer material of the scaffold during spinning. The scaffold can be treated while oriented in the solvent horizontally, vertically, at an angle or in a combination of orientations to achieve a desired shaping.

In one embodiment, the scaffold rotates around its own axis and revolves around in a chamber with solvent to control the shaping of the scaffold structure cross section.

As an alternative to spinning or rotating the scaffold, the solvent media can flow relative to the scaffold, or a combination of rotating the scaffold and causing solvent to flow can be used to achieve the desired effect. In another embodiment, the scaffold and the solvent both move relative to each other. Examples of this would be a revolving scaffold on a rotating mandrel in a solvent bath which is being stirred with a stir bar.

Figure 10:
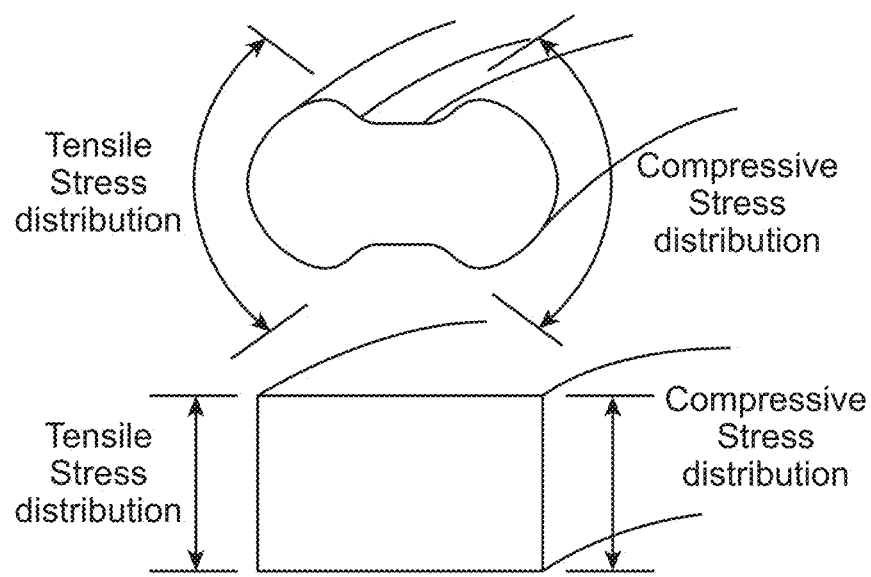
FIG. 10 is a schematic illustration of the difference in tensile and compressive stress distribution between a treated and untreated stents (as formed stents)

FIG. 2 illustrates a cross section of a strut after treatment according to one example. In this figure, the treatment provides a concave abluminal surface across substantially the width of the surface; it also provides convex side surfaces across the thickness of the surfaces. These shapes allow the distribution of tensile and compressive stresses over a greater area as shown in FIG. 10. As shown in FIG. 10, the surface area over which the tensile and compressive stresses are distributed during bending of the strut is increased due to the convex side surfaces and this leads to increased radial strength of the scaffold. In one embodiment, a scaffold with modified cross section has increased radial strength by at least 5%, at least 10% or at least 20% over scaffolds without modified cross section. The treatments described herein can increase the radial strength of the scaffold by at least 5%, at least 10% or at least 20%.

The first and second solvents and the processes for dipping and removing solvent can vary depending on the desired scaffold cross sectional shape.

One advantage of the abluminal shaping is the increased drug delivery to the walls of the lumen which can be achieved with a concave abluminal surface. The abluminal concave surface can help direct drug delivery to the lumen wall. This focused drug delivery using concave abluminal surfaces.

b. Luminal and Side Shaping by Solvent Dipping

Shaping of or enhancing the luminal shape and/or shaping the side surfaces of the scaffold struts, crowns and other structures without abluminal shaping can be achieved by placing a tube such as Teflon tube over the scaffold. The outer tube should be tight fitting so that no significant amount of fluid can pass between the outer surfaces of the scaffold and the inner surface of the tube. Optionally, a looser mandrel such as a Teflon rod or tube can be inserted inside the scaffold as a support for handling purposes. Preferably, the outer diameter of this looser inner mandrel is 0.001" to 0.100" smaller, more preferably 0.005" to 0.015" smaller than the inner diameter of the scaffold. The scaffold sheathed with the outer tube and supported lightly on the inner mandrel is then dipped into a first solvent for about 1 sec and quickly removed and preferably rinsed in a second solvent to remove materials that are adhering to the scaffold according to any of the methods and with any of the solvents described above with respect to the previous processes.

Figure 11:
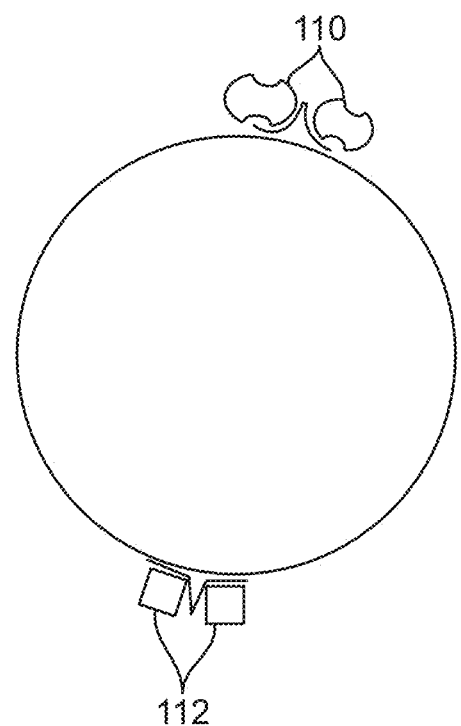
FIG. 11 is a schematic cross section of a balloon showing a pair of struts having modified/treated surfaces and a pair of struts having unmodified surfaces.

Shaped luminal surfaces and shaped side surfaces can provide an improved surface for contact with a delivery system, such as a balloon catheter. The convex side surfaces provide greater contact than square or rectangular flat surfaces between balloon material of the delivery system and the scaffold. FIG. 11 illustrates a balloon with a pair of struts 110 having modified luminal surfaces and convex sides and a pair of struts 112 having flat surfaces. In the process of crimping the scaffold onto the balloon a portion or flap of balloon material extends between the struts. As can be seen in FIG. 11, there is increased surface area of contact between the modified struts 110 with convex sides and the balloon flap than with the flat surfaces of the struts 112. This provides improved scaffold retention on a balloon catheter in a crimped configuration by using a shaping processing step.

Additionally, the concave luminal surfaces of the scaffold structures can also improve stent retention on a balloon or other delivery system by providing a form of suction or vacuum surface which adheres the modified scaffold better to the balloon.

c. Solvent Vapor Shaping

The scaffold can be exposed to vapors of a solvent for an amount of time sufficient to provide a desired shaping of the scaffold structures. In the solvent vapor shaping method, the scaffold is placed adjacent to a bath of liquid solvent in a solvent chamber. The solvent is selected to be a solvent which can dissolve the scaffold at least in part if the scaffold is placed in the solvent for one minute. However, in this method, it is the vapors from the solvent which come in contact with the crowns, axial struts and other portions of the scaffold and redistribute the material of the scaffold to provide convex side surfaces, concave luminal and/or abluminal surfaces. The solvent or the entire vapor chamber can be heated to accelerate vaporization of the liquid solvent in the liquid bath. Alternatively, the solvent vapor can be provided into the chamber in a gaseous form alone or with other gases. The time of exposure of the scaffold to solvent vapor can be greater than 10 mins, greater than 30 mins, greater than 1 hour, greater than 24 hours, or greater than 48 hours.

In one embodiment, the scaffold rotates around its own axis and revolves around in a chamber with solvent vapor to control the shaping of the scaffold structure cross section.

After the solvent vapor shaping process is complete, excess solvent can be removed by a second solvent, heating, drying or any of the methods discussed herein. In one example, the solvent chamber can be pressurized to increase the amount of solvent vapor in contact with the scaffold.

The exposure of only a portion of the scaffold to the solvent vapor, such as by inserting a tight tube inside the scaffold or inserting the scaffold inside a tight tube can preferentially shape the surfaces on the luminal or abluminal sides of the scaffold. Other masking methods can also be used.

The solvents employed in the solvent vapor smoothing process can include any of the solvents described above. Particularly useful solvents are those that can be provided in a gaseous form at a temperature of less than the Tg of the scaffold material.

d. Solvent Spraying

The scaffold can be exposed to solvent by spraying with the solvent to shape the surfaces of the struts, crowns and other scaffold structures and redistribute the scaffold material. Spraying of solvent can be performed with any spray apparatuses, such as those that are known for application of drug/polymer coatings to stents. The sprayed solvent may be any of the solvents described herein which are capable of dissolving a portion of the scaffold structure.

Solvent spraying from an exterior of the scaffold can result in preferential shaping with the abluminal strut surfaces experiencing greater concave shaping than the luminal surfaces. In one example, abluminal surfaces have a concave radius of curvature greater than luminal surfaces. Solvent spraying can also be from an interior of the scaffold by passing a spray nozzle into the interior of the scaffold and moving it along the length of the scaffold interior. Masking of portions of the scaffold may also be used to get preferential shaping of some surfaces over other surfaces.

In one example, a flow rate of solvent sprayed onto the scaffold is higher than typically use for coating a stent. Flow rates of at least 20 ul/min, at least 30 ul/min, or preferably at least 75 ul/min, or more preferably at least 100 ul/min can be used.

A loose mandrel can be placed inside the scaffold during spraying to maintain the shape of the scaffold as the solvent is sprayed onto the surfaces.

The scaffold can be rotated and/or moved longitudinally during spraying. In one example, the scaffold is rotated and moved in a crisscross fashion during spraying to achieve uniformity of shaping and to prevent large amounts of material from being dissolved or redistributed too quickly. Air can be blown at the scaffold to remove any excess solvent during and/or after spraying of the solvent. Removal of excess solvent can be performed by any of the processes described herein.

e. Other Solvent Application

In addition to application of solvent by dipping, spraying, or application of solvent vapor, solvent can be applied to a scaffold to provide shaped scaffold in other manners including ink jet printing, painting, gel application or the like.

Some of the solvent application methods described herein can apply solvent only to portions of the scaffold while leaving other portions of the scaffold untreated such as preferentially shaping and/or smoothing only the luminal or only the abluminal surfaces. In another example, the treatment is applied only to the crowns to further enhance the convex side surfaces of the crowns as these are the areas most likely to affect tracking of the stent through the vasculature. The treatment can also be used to preferentially treat different longitudinal sections of the scaffold to achieve a scaffold with differing performance along its length. In one example, the ends of the scaffold are treated to achieve a scaffold with greater radial strength at the scaffold ends.

2. Media Blasting.

Shaping of the scaffold surfaces can also be performed by material removal or material compacting from the scaffold by various media blasting techniques. Material removal from or compacting of the scaffold crowns or axial struts of a scaffold to create convex side surfaces, and concave abluminal surfaces can be achieved using equipment such as a sandblaster, media blasting machine, or similar equipment which propels particles at the scaffold. The blasting treatment propels small, abrasive particles toward the scaffold in a particular pattern which matches the regions of the scaffold to be shaped.

Examples of particles which can be used include evaporable particles, such as dry ice, salt, sugar, sodium bicarbonate, combination thereof, or the like which will either vaporize or can dissolve in water. The use of dry ice or another evaporable particle as the media particles which will turn gaseous at ambient temperature eliminates the need for removal of the blasting particles after the surface shaping process. In some examples, the evaporation of the evaporable particles may be assisted by application of heat, vacuum, or the like. The use of dry ice as the media particles can eliminate the need for removal after the shaping process because the dry ice will turn gaseous at ambient temperature.

Other blasting media can include polymeric particles such as polyethylene, polypropylene, polyethylene glycol, polyvinyl alcohol, polyvinylacetate, polyvinyl chloride, cellulose, copolymers of these, combination thereof, or the like which will dissolve in a solvent that does not immediately dissolve the scaffold such as ethanol, methanol, propanol, THF, acetone, or the like. Exposure to solvent after blasting with polymeric particles can remove particles that become at least partially embedded on the surface of the scaffold. The media particles preferably can dissolve in a solvent in a period of less than 1 minute and the solvent is selected such that the scaffold does not dissolve in the solvent when the scaffold is exposed to solvent for 1 minute or longer.

A size of the blasting particles using screened mesh sizing can range from 60 to 600 mesh, from 100 to 550 mesh, or preferably from 150 to 500 mesh.

The size of the blasting particles impacting the surface of the scaffold range from 250 microns to 10 microns, preferably from 100 microns to 20 microns, more preferably from 50 microns to 25 microns.

In one example, instead of focusing the blasting particles on the edge during sandblasting, a mask can cover the majority of the scaffold surface but exposes only a portion of the edges of the crowns or axial strut. The mask can be applied by ink jet printing technologies. The covered scaffold is then sandblasted to remove only material on the edge. Preferably sandblasting is done at an angle. The mask can then be removed by any known means, such as by application of a solvent which dissolves the mask without dissolving the scaffold. After removal of the mask the resulting convex side surfaces and concave luminal and abluminal surfaces are exposed.

In one embodiment, the media blasting compacts the material to provide the desired shapes without removing a substantial amount of the polymeric material from which the stent is formed.

3. Abrasive Tumbling

In one embodiment, the scaffold surfaces can be shaped by abrasive tumbling methods. The scaffold can be placed in a tumbler, shaker, or vibrator with a lapping media, a sandblasting media, abrasives, abrasive grit, liquid lubricants, dry ice, others, or combination thereof, to form concave abluminal surface having radii of curvatures of about 0.030 to about 0.200 mm, about 0.040 to about 0.150 mm, or about 0.040 to about 0.100 mm Examples of abrasive media include aluminum oxide, jeweler's rouge, optician's rouge, emery, silicon carbide, diamond, glass, metal, oxides, ceramics, or the like. In the abrasive tumbling methods, one or more scaffolds are placed inside a barrel or tumbler which is placed on slowly rotating rails which rotates, shakes, or vibrates the barrel. The scaffolds within the barrel slide past each other, with the lapping media, sandblasting media, abrasives, abrasive grit, liquid lubricants, others, or combination thereof, between them. The amount and speed of the shaping depends on the coarseness of the abrasive, and the duration of the tumble, shaking, or vibrating.

In one embodiment, the scaffolds can be cooled to make the material more brittle. The scaffold can be cooled to a temperature below 10 degrees Celsius, preferably below 0 degrees Celsius, more preferably below −50 degrees Celsius using dry ice or liquid nitrogen before and/or during tumbling.

In one embodiment, the scaffolds can be heated to make the material softer. The scaffold can be heated to a temperature above Tg before and/or during tumbling.

In one example, a mask can be applied by ink jet printing technologies or another known process to allow selective abrasive shaping of the scaffold surfaces. The masked scaffold is then tumbled to remove only material on the selected portions. The mask can then be removed by any known means, such as by application of a solvent which dissolves the mask without dissolving the scaffold. After removal of the mask the resulting convex side surfaces and concave luminal and abluminal surfaces are exposed. As in the other shaping processed described herein, selective portions of the scaffold can be shaped without shaping other portions of the scaffold by use of mandrels, sleeves and/or masking.

4. Mechanical Shaping, Molding and Ink Jet Printing.

The surfaces of crowns, axial struts, or other portions of a scaffold can be shaped or chamfered by certain mechanical tools to form shaped surfaces. The surfaces can be shaped or chamfered with a miniature tool having a sharp edge or deburring brush and small enough to fit between crowns and axial struts and scraping the tool across the surfaces. These tools can be moved robotically and controlled by a camera and an image processing system.

In another example, the tool can be a rotating miniature sanding tool which by spinning against the surfaces or edges of the crowns or axial struts creates convex side surfaces, concave luminal surfaces and/or concave abluminal surfaces.

In order to increase the hardness of polymer scaffolds or other scaffolds of soft materials for mechanical shaping according to any of the described processes, the scaffold can be held at a temperature below 10 degrees Celsius, preferably below 0 degrees Celsius, more preferably below −50 degrees Celsius using dry ice or liquid nitrogen.

The abluminal surfaces of the crowns of a scaffold can be shaped or chamfered by inserting a curved or flexible mandrel inside the scaffold. The scaffold in the curved position on the mandrel is then dragged over an abrasive material such as sandpaper wrapped around a cylinder, round file, deburring brush, sanding stone, or the like. As the scaffold in a curved position is abraded against the surface of the abrasive means, the leading edge of the crowns will be chamfered, beveled or deburred.

An inside surface of the scaffold can be processed to shape the luminal surfaces of the crowns, struts and other structures by inserting a flexible abrasive means through the interior of the scaffold.

Ink jet printing technologies can also be used to build up some portions of the scaffold to achieve concave luminal and abluminal surfaces and convex side surfaces of the scaffold structures.

Molding, over molding or compression of a preformed part in a shaped mold can also be used to form the scaffold with the shaped concave luminal and abluminal surfaces and convex side surfaces of the scaffold structures or to treat a scaffold to form the concave luminal and abluminal surfaces and convex side surfaces.

5. Laser Shaping.

A laser can be used to shape the scaffold structures. With a laser having the ability to ablate with low energy and layer by layer, such as a femtosecond laser, a laser cutting program can be set to ablate a desired shape of the scaffold surfaces. In one example, the laser can be used to create concave luminal and abluminal surfaces and convex side surfaces of the scaffold structures. A series of laser formed steps can create the convex side surfaces of the struts. In a similar manner, the laser can be used to create the concave luminal or abluminal surfaces by a series of small steps along the surface. The steps can be smoothed out with solvent, sandblasting, tumbling, or the like.

In one example, a series of overlapping cuts, with each cut narrower than 35 micrometers, narrower than 30 microns, or narrower than 25 microns can be made from the abluminal surface to the side surface of the scaffold to achieve the convex side surface on the crown, axial strut or other structure.

In another example, the scaffold can be cut during the laser cutting process with off-axis control such that the axis of the laser beam and the axis of the assist gas supply nozzle on the laser such as a femtosecond laser is eccentrically oriented. This allows the laser to cut material at an angle rather than straight cut, resulting in a curved surface. This process can be used to form the curved surfaces described herein.

The convex side surfaces of the scaffold can also be formed using either trepanning or helical drilling Trepanning is a combined cutting and drilling process, typically performed using a pulsed laser. In trepanning, a through hole is first pierced by percussion drilling and then in a second step the through hole is widened to its final diameter in a circular cutting motion by the laser. In a similar manner, the laser beam can cut the material at an angle to form the curved surfaces. After a first cut at an angle to form the rounded top portion of the strut side surfaces, the laser can cut the rest of the scaffold pattern with a straight cut. This results in a partially convex side surface. It is also possible to make the last part of the laser at an angle so that side surface is fully convex. In helical drilling, a rotational movement of the laser beam is used to create a positive or negative taper at the scaffold surfaces.

6. Heat Shaping

In another example, the surfaces of scaffold can be melted by thermal energy and the material can be redistributed to achieve the desired shaping of the surfaces. In the thermal method heat may be applied in an oven, for a duration and at a temperature to provide convex side surfaces and/or concave luminal and abluminal surfaces. The heating temperature can be controlled to reach the melting temperature of the polymer at the surfaces regions to be shaped without reaching the melting temperature in the remainder of the scaffold material.

The convex side surfaces can also improve flexibility of the scaffold or stent. The scaffold with curved axial struts can bend in a multitude of directions compared to axial struts with flat surfaces. For example, a scaffold with rectangular axial struts or links will bend primarily in two preferred directions because of the flat surfaces of the axial struts. The struts cannot bend in the direction of the edge. However, modified strut cross sections with convex sides provide more freedom to bend in multiple directions and thus provide a more flexible and deliverable stent or scaffold.

When the struts, crowns and other scaffold structures are coated with a drug for delivery to a lumen, the convex side surfaces of the scaffold can provide for a more uniform drug coating and thus can release drug from a substantially more uniform surface than a square or rectangular strut. The concave luminal and abluminal surfaces also can provide improved directionality of drug delivery to the lumen or vessel wall.

For a substantially amorphous polymer material which is less than 15%, preferably less than 10% crystalline, solvent shaping of the tubular body does not significantly alter the crystalline orientation of the material since the substantially amorphous material is random in crystalline orientation.

Figure 12:
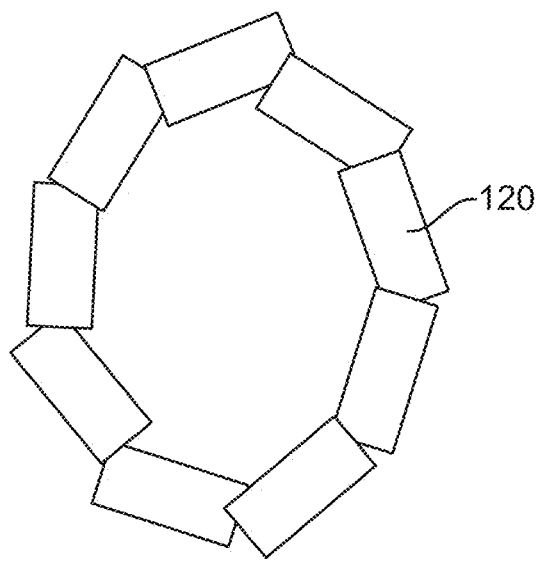
FIG. 12 is a cross section of a crimped stent having unmodified side surfaces.
Figure 13:
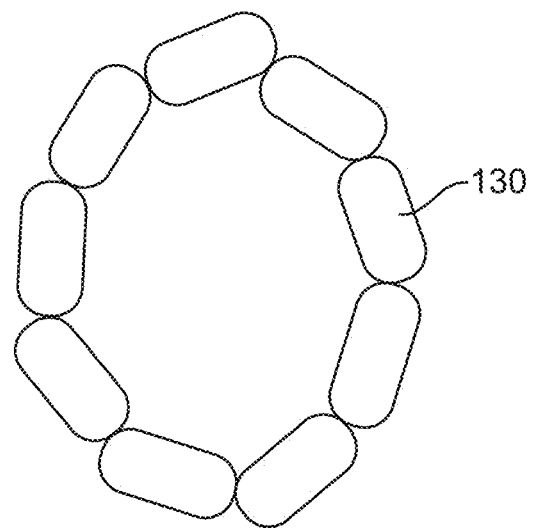
FIG. 13 is a cross section of a crimped stent having modified side surfaces.

The convex side surfaces can also improve crimping of the scaffold or stent because convex structure sides are more resistant to overlapping struts when crimped from a larger as-cut diameter to a smaller crimped diameter due to the absence of flat surfaces which can catch on one another during crimping. FIG. 12 illustrates an end view of a crimped stent with rectangular struts 120. The rectangular struts 120 can overlap and twist due to crimping. The struts 130 of FIG. 13 having curved side surfaces can reduce or eliminate the overlapping and twisting which occurs with flat rectangular surfaces. FIG. 13 shows the stent structures in cross section with convex side surfaces. Twisting and rotating of struts, crowns or links along their axis can happen during expansion as well as during crimping. The convex side surfaces and concave abluminal surfaces prevent or reduce rotating of struts during crimping and/or during expansion to less than 45 degrees, less than 35 degrees or less than 25 degrees.

Struts or other scaffold structures having shaped surfaces as described above can be considered to have oblong, oval, elliptical, near elliptical, circular, near circular, or dogbone like cross sectional shapes. Where the shaping treatment is performed before application of the drug in a preferred embodiment, the drug coating process achieves a product with shaped surfaces as the coating process maintains substantially the same shape.

In one embodiment, the biodegradable stent prosthesis comprises a body having a plurality of rings each ring comprises a plurality of struts joined by crowns, wherein each ring is connected to an adjacent ring by at least one link.

In another embodiment, the biodegradable stent prosthesis comprises a body having a plurality of struts joined by crowns.

In yet another embodiment, the biodegradable stent prosthesis comprises a body having a plurality of rings connected by at least one link, and a plurality struts joined by crowns.

In another embodiment, the biodegradable stent prosthesis comprises a body having one luminal, one abluminal surface, and two side surfaces, along the length of the stent prosthesis.

In another embodiment, the biodegradable stent prosthesis comprises a body having abluminal surfaces, luminal surfaces, and two side surfaces of each structural component of the stent, along the length of the stent.

In another embodiment, the biodegradable stent prosthesis comprises a polymeric material forming a tubular body, wherein said body comprises a stent pattern having a plurality of struts, crowns and optionally links, each having four surfaces, such that a cross section of said struts is rectangular having a concave abluminal surface and/or convex side surface, and a cross section of said crown is substantially rectangular having convex side surfaces and/or optionally a concave abluminal surface. The cross-section is substantially rectangular in the sense that the dimensions of width and thickness are different.

In another embodiment, the biodegradable stent prosthesis comprises a polymeric material forming a tubular body, wherein said body comprises a stent pattern having a plurality of struts, crowns and optionally links, each having four surfaces, such that a cross section of said struts is substantially square having concave abluminal surfaces, and/or convex side surfaces, and a cross section of said crown is substantially square having convex side surfaces, and/or optionally concave abluminal surface. The cross-section is substantially square in the sense that the dimensions of width and thickness are substantially the same.

In another embodiment, the biodegradable stent prosthesis is expandable from a crimped configuration to an expanded larger configuration to support a body lumen or a blood vessel.

In another embodiment, the biodegradable stent prosthesis is expandable from a crimped configuration to an expandable larger configuration at body temperature.

In another embodiment, the biodegradable stent prosthesis is expandable from a crimped configuration to an expandable larger configuration and have sufficient strength to support a body lumen or a blood vessel.

In another embodiment, the biodegradable stent prosthesis is circumferentially expandable from a crimped configuration to an expanded larger configuration.

In another embodiment, the biodegradable stent prosthesis comprises a biodegradable polymeric material.

In another embodiment, the biodegradable stent prosthesis comprises a biodegradable metal or metal alloy.

In another embodiment, the biodegradable stent prosthesis comprises a biodegradable polymeric material, and a biodegradable metal or metal alloy.

In another embodiment, the biodegradable prosthesis comprises a degradable polymeric material, said polymeric material is formed as a tubular body using extrusion, dipping, spraying, or printing.

In another embodiment, the biodegradable stent prosthesis comprises a degradable metal or metal alloy, said metal or metal alloy is formed as a tubular body.

In one embodiment, an expandable biodegradable prosthesis comprises an expandable prosthesis body formed from a biodegradable polymeric material, the expandable prosthesis body having a plurality of stent structures each having luminal and abluminal surfaces. The plurality of stent structures include a plurality of circumferentially expandable serpentine rings, each serpentine ring including axial struts joined by crowns. At least some of the stent structure abluminal surfaces are concave across substantially the width of the stent structure. The prosthesis is expandable from a crimped configuration to an expanded larger configuration to support a body lumen.

In another embodiment, the biodegradable stent prosthesis comprises a degradable polymeric material formed as a tubular body, said stent is patterned into a structure comprising a plurality of rings, wherein each ring comprises a plurality of struts and crowns, wherein adjacent rings are connected by at least one link, wherein the stent struts have abluminal and luminal surfaces, wherein at least some of the struts abluminal surfaces are concave across substantially the width of said struts.

In another embodiment, the biodegradable stent prosthesis comprises a degradable polymeric material formed as a tubular body, said stent is patterned into a structure comprising a plurality of rings, wherein each ring comprises a plurality of struts and crowns, wherein adjacent rings are connected by at least one link, wherein the stent struts have abluminal and luminal surfaces, wherein substantially all of the struts abluminal surfaces are concave across substantially the width of said struts.

In another embodiment, the biodegradable stent prosthesis comprises a degradable polymeric material formed as a tubular body, said stent is patterned into a structure comprising a plurality of rings, wherein each ring comprises a plurality of struts and crowns, wherein adjacent rings are connected by at least one link, wherein the stent struts have abluminal and luminal surfaces, and at least one side surface between the luminal and abluminal surfaces, wherein at least some of the struts abluminal surfaces are concave across substantially the width of said struts, and wherein at least some of the struts side surfaces are convex across substantially the thickness of said struts.

In one embodiment, the biodegradable stent prosthesis is patterned into a structure comprising a plurality of serpentine rings, each ring comprises struts joined by crowns, and wherein adjacent rings are joined by at least one link, said rings have abluminal and luminal surfaces, and two side surfaces between the luminal and abluminal surfaces; wherein at least some of the rings luminal surfaces are concave across substantially the width of said ring, and wherein at least some of the rings side surfaces are convex across substantially the thickness of said ring.

In another embodiment, the stent structures comprise side surfaces extending between the luminal and abluminal surfaces, wherein at least some of the side surfaces are convex.

In a further embodiment, the expandable prosthesis body is formed from a tube and the formed prosthesis body has been treated to form the concave abluminal surfaces.

In a further embodiment, the expandable prosthesis body is formed from a flat sheet and the formed prosthesis body has been treated to form the concave luminal and abluminal surfaces.

In another embodiment, the treatment does not substantially change the weight of the prosthesis body.

In another embodiment, the stent prosthesis is treated to form concave shapes across substantially the width of the stent abluminal surfaces, and convex shapes across substantially the thickness of the stent side surfaces, wherein the weight of the stent prosthesis before treatment and after treatment is substantially the same.

In another embodiment, the stent prosthesis is treated to form concave shapes across substantially the width of the stent abluminal surfaces, and convex shapes across substantially the thickness of the stent side surfaces, wherein the weight of the stent prosthesis before treatment and after treatment are within 15% of each other.

In another embodiment, the stent prosthesis is formed comprising concave shapes across substantially the width of the stent abluminal surfaces, and convex shapes across substantially the thickness of the stent side surfaces, and wherein the weight of the stent prosthesis before treatment and after treatment is substantially the same.

In one embodiment, a method of forming an expandable polymer prosthesis with modified surfaces includes the steps of forming a tubular expandable prosthesis with a plurality of stent structures each having a luminal surface, an abluminal surface and two side surfaces extending between said luminal and abluminal surfaces by patterning the prosthesis from a polymer tube; and exposing the expandable prosthesis to a treatment for a predetermined period of time to modify the surfaces, wherein resulting modified abluminal surfaces are concave.

In another embodiment of the method the modified side surfaces of the expandable prosthesis are convex.

In a further embodiment of the method the treatment changes the shapes of the surfaces and does not substantially change the weight of the prosthesis.

In one embodiment, an expandable prosthesis includes an expandable prosthesis body formed from a plurality of stent structures including struts, crowns and optionally links, each having luminal and abluminal surfaces and side surfaces extending between the luminal and abluminal surfaces, wherein at least some of the abluminal surfaces are concave and wherein at least some of the side surfaces are convex, wherein said prosthesis is expandable from a crimped configuration to an expanded larger configuration to support a body lumen.

In one example, the endoprosthesis is patterned from a tube by laser cutting and the laser cut treatment forms the concave abluminal surfaces and convex side surfaces. In some embodiments, the treatment comprises shaping by application of a solvent by at least one of dipping, spraying, or contact with a solvent vapor.

In another example, the treatment includes shaping by tumbling, agitating, deburring, scraping, or sandblasting. In a further example, the processing includes shaping with a laser or heat. The processing can be followed by forming a coating of at least one drug formed over the expandable endoprosthesis body.

In another example, the endoprosthesis stent structures comprises a plurality of circumferentially expandable serpentine rings, each serpentine ring comprises axial struts joined by crowns, wherein one crown joins two adjacent axial struts of a serpentine ring, and wherein the crowns act as hinges allowing the struts to spread as the ring expands circumferentially, at least one link joining adjacent serpentine rings.

In one embodiment, the stent endoprosthesis is formed from a biodegradable polymeric material which has a molecular weight ranging from 100 KDa to 1000 KDa. In another embodiment, the biodegradable polymeric material has an elastic modulus of at least 0.35 Gpa, preferably between 0.35 Gpa and 1.5 Gpa.

The biodegradable polymeric material comprises one or more of polymers and copolymers. In one embodiment, the endoprosthesis is capable of being expanded from a crimped diameter to a deployed diameter at body temperature without fracture of the endoprosthesis.

In another embodiment, the endoprosthesis comprises a biodegradable polymeric material comprising one or more of: Lactide, poly-DL-Lactide, polylactide-co-gycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

In another embodiment, the polymeric material comprises one or more polymers or co-polymers, or polymer blends.

In a further embodiment, the prosthesis body is formed as a tube and patterned by laser cutting.

The endoprosthesis is preferably balloon expandable.

In another embodiment, the endoprosthesis is self-expandable.

In another embodiment, the stent prosthesis is self-expandable and balloon expandable.

In another embodiment, a polymer endoprosthesis comprises a tubular expandable endoprosthesis body comprising a polymeric material which has been patterned from a tube to form the stent, said stent comprises a plurality of struts each strut having a luminal surface, an abluminal surface, and two side surfaces extending between said luminal and abluminal surfaces, wherein at least one of the abluminal surfaces is concave, and wherein the two side surfaces are convex.

In a further embodiment, a drug coating comprising at least one drug is coated on at least a portion of the expandable endoprosthesis body. In another embodiment, the at least one drug is contained within a coating, preferably a polymeric coating, covering at least a portion of the stent prosthesis.

In another embodiment, a method of forming a polymer endoprosthesis prosthesis with modified surfaces comprises the steps of forming a tubular expandable endoprosthesis with a plurality of struts each having a luminal surface, an abluminal surface and two side surfaces extending between said luminal and abluminal surfaces by cutting the endoprosthesis from a polymer tube and exposing the tubular expandable endoprosthesis to a treatment for a predetermined period of time to modify the surfaces, wherein the resulting modified abluminal surfaces are concave while the modified two side surfaces are convex.

In some embodiments, at least some of the abluminal surfaces of some portions of the polymeric prosthesis are concave and at least some of the side surfaces are concave.

In another embodiment substantially all of the abluminal surfaces of the prosthesis are concave and substantially all of the side surfaces of the prosthesis are convex.

In one method, the treatment changes the shapes of the surfaces and does not substantially change the weight of the endoprosthesis.

In another method, the treatment does not significantly dissolve the polymeric material from which the endoprosthesis is formed.

In another method, the treatment does not substantially dissolve the polymeric material from which the endoprosthesis is formed.

In a preferred embodiment, the treatment shift polymeric material from at least one surface to an adjacent surface without substantial change in weight before and after treatment.

In a preferred embodiment, the treatment shift polymeric material from at least one surface to an adjacent surface modifying at least some abluminal surfaces into concave shape and at least some side surfaces into convex surfaces without substantially change in the weight before and after treatment.

In another embodiment, the treatment shifts polymeric material from abluminal and/or luminal surfaces of the stent prosthesis to the side surfaces of the stent prosthesis (or vice versa), preferably without substantially loss of material, more preferably without weight change of more than 5%, most preferably without substantial change in stent weight.

In another embodiment, the treatment shifts polymeric material from at least one side surface to one of luminal or abluminal surfaces of the stent prosthesis, preferably without substantially loss of material, more preferably without loss of more than 5%, most preferably without substantial change in stent weight.

In a further embodiment, a method of forming a polymer endoprosthesis prosthesis with a controlled strut thickness includes the steps of forming a tubular expandable endoprosthesis with a plurality of struts by cutting the endoprosthesis from a polymer tube having a first thickness, said endoprosthesis comprising a polymeric material and exposing the tubular expandable endoprosthesis to a solvent for a predetermined period of time to redistribute said polymeric material without substantially dissolving it to adjust a thickness of the plurality of struts to a second thickness, wherein the second thickness is greater than the first thickness.

In another embodiment, a polymer endoprosthesis includes a tubular expandable endoprosthesis body comprising a polymeric material which has been cut from a tube to form an endoprosthesis with a plurality of struts each having a luminal surface, an abluminal surface, and two side surfaces extending between said luminal and abluminal surfaces, wherein the two side surfaces are convex and have a radius of curvature of at least 0.020 mm In a further embodiment, a polymer endoprosthesis comprises a tubular expandable endoprosthesis body comprising a polymeric material which has been cut from a tube to form an endoprosthesis with a plurality of struts each having a luminal surface, an abluminal surface, and two side surfaces extending between said luminal and abluminal surfaces, wherein the abluminal surfaces of the struts are shaped to form concave surfaces extending substantially from one side surface to an opposite side surface; a coating comprising at least one drug formed over the tubular expandable endoprosthesis body. In a preferred embodiment a coating comprising a drug is coated over said abluminal surface without substantially changing the concave shape.

In another embodiment, a method of forming a polymer endoprosthesis prosthesis with a modified shape includes the steps of forming a tubular expandable endoprosthesis with a plurality of struts having luminal, abluminal and side surfaces extending between said luminal and abluminal surfaces by cutting the endoprosthesis from a polymer tube having a first thickness and treating the tubular expandable endoprosthesis to increase a thickness of the plurality of struts between the luminal and abluminal surfaces while decreasing a width of the struts between the side surfaces by redistributing the polymer. In another embodiment, the treating increases the thickness of a plurality of struts but the width of the struts remains unchanged.

In another embodiment, the biodegradable stent prosthesis, comprising a biodegradable polymeric material formed as a tubular body, wherein said tubular body is composed of an abluminal surface, a luminal surface, and two side surfaces, wherein the tubular body is patterned into a structure having an abluminal surface, a luminal surface, and side surfaces, and wherein the stent is treated after patterning to shift polymeric material from at least one side surface to said luminal and/or abluminal surfaces.

In another embodiment, the biodegradable stent prosthesis, comprising a biodegradable polymeric material formed as a tubular body, wherein said tubular body is composed of an abluminal surface, a luminal surface, and at least two side surfaces, wherein the tubular body is patterned into a structure having an abluminal surface, a luminal surface, and at least two side surfaces, and wherein the stent is treated after patterning to shift polymeric material from at least some luminal and/or abluminal surfaces to at least one adjacent side surface, wherein the at least said treated abluminal surfaces become substantially concave, and wherein the at least adjacent side surfaces become substantially convex.

In another embodiment, the biodegradable stent prosthesis, comprising a biodegradable polymeric material formed as a tubular body, wherein said tubular body is composed of an abluminal surface, a luminal surface, and at least two side surfaces, wherein the tubular body is patterned into a structure having an abluminal surface, a luminal surface, and at least two side surfaces, and wherein the stent is treated after patterning to shift polymeric material from at least some side surfaces to at least one adjacent luminal and/or abluminal surface (or vice versa shifting material from luminal and/or abluminal to side), wherein the at least some treated abluminal surfaces become substantially concave, and wherein the at least some adjacent side surfaces become substantially convex, and wherein the weight of the stent prosthesis before and after said treatment is substantially the same.

In another embodiment, the biodegradable stent prosthesis, comprising a biodegradable polymeric material formed as a substantially flat body, wherein said body is composed of an abluminal surface, a luminal surface, and at least two side surfaces, wherein the body is patterned into a structure having an abluminal surface, a luminal surface, and at least two side surfaces, and wherein the stent is treated after patterning to shift polymeric material from at least some side surfaces to at least on adjacent luminal and/or abluminal surface, wherein the at least said treated luminal and/or abluminal surfaces become substantially concave, and wherein the at least adjacent side surfaces become substantially convex, and wherein the weight of the stent prosthesis before and after said treatment is substantially the same.

In another embodiment, the surface roughness of treated luminal, abluminal, and adjacent sides, are substantially reduced after treatment. In one embodiment, the surface roughness of treated luminal, abluminal, and adjacent side surfaces, are substantially reduced after process treatment. In one embodiment the root-mean-square roughness (Sq) ranges between 0.5 microns to 15 microns. In another embodiment the roughness average (Sa) ranges from 0.5 microns to 10 microns as measured by optical profilometry or atomic force microscopy.

In another embodiment, the treated surfaces increase crystallinity at the surface of the stent prosthesis by at least 15%.

In another embodiment, the treated surface has a crystallinity that is substantially different from the core of the treated stent prosthesis by at least 15%, or by at least 20%, or by at least 25%, or by at least 30%. The crystallinity of the treated surface within 25% depth from the treated surface is substantially different from the crystallinity of the said core of the treated stent prosthesis.

In another embodiment, the treated surfaces increase cross linking at the surface of the stent prosthesis. Increased cross linking results in a scaffold which absorbs less solvent when exposed to the solvent. The increase in cross linking results in absorption of solvent reduction by at least 10%.

In another embodiment, the treated stent prosthesis surface has an increased hydrophobicity. This is very helpful when coating the stent prosthesis with a coating or a drug comprising a solvent wherein the absorption of said solvent is reduced by at least 10%. It can also be helpful to delay substantially complete hydration of the stent prosthesis by at least 1 minute.

When fabricating a biodegradable stent prosthesis, it is desirable to design the prosthesis such that the stent design comprising crowns or/and struts, having width to thickness dimensions that are approximately 1:1, or range from approximately 0.8:1 to approximately 1.1:1, such that upon expansion of the biodegradable stent prosthesis said struts and crowns along the length of the stent prosthesis are substantially free from rotating around their axis, or substantially free from rotating more than 45 degrees around their axis. This allows the stent prosthesis to have improved strength such as sufficient strength to support a body lumen, improved uniformity of expansion, and/or be free from fracture upon expanding the stent from a crimped configuration to an expanded larger configuration.

However, such desire is difficult to achieve when using biodegradable material since the biodegradable material are typically weaker material and therefore in order to achieve smaller thickness, the width of such stent prosthesis struts will be larger than thickness, typically width to thickness ratio are at least 1.2:1, and that contributes to having struts along the length of the stent prosthesis prone to rotating or twisting upon expanding the stent prosthesis from a crimped configuration to an expanded larger configuration, resulting in lower strength, lower uniformity of expansion, or strut and/or crown fracture, upon expansion of the stent or after expansion. It is therefore desirable to be able to design a biodegradable stent prosthesis that is smaller in thickness, having a width to thickness ratio of at least 1.2:1 wherein the stent struts upon expansion or after expansion are substantially free from said struts and/or crowns rotating, or substantially free from rotating more than 45 degrees around their axis, or substantially free from rotating more than 25 degrees around their axis. Such desire for performance is achieved when fabricating a stent comprising stent struts and/or crowns that have at least some of the luminal and/or abluminal surface concave, and optionally at least some of the sides extending between said luminal and abluminal surfaces convex, said degradable stent prosthesis struts and/or crows upon expansion from crimped configuration to an expanded configuration are substantially free from rotating more than 45 degrees around their axis.

In another embodiment, the biodegradable stent prosthesis comprises a biodegradable polymeric material formed as a tubular body using extrusion, dipping, spraying or printing, wherein the stent prosthesis is patterned into a structure comprising struts wherein said struts having widths that are at least 1.2 times said struts thickness, wherein the patterned structure comprises luminal, abluminal, and side surfaces, wherein at least some of said struts having concave abluminal surfaces along the width of said struts, and optionally wherein at least some of said struts have at least one convex side surface extending between said abluminal and luminal surface, said stent prosthesis is expandable from a crimped configuration to an expanded larger configuration wherein the said struts remain substantially free from rotating.

In one embodiment, an expandable prosthesis includes an expandable prosthesis body formed from a plurality of stent structures each having luminal and abluminal surfaces and side surfaces extending between the luminal and abluminal surfaces, wherein at least some of the luminal and abluminal surfaces are concave and wherein at least some of the side surfaces are convex, wherein said prosthesis is expandable from a crimped configuration to an expanded larger configuration to support a body lumen.

In one example, the endoprosthesis is cut from a tube by laser cutting and the laser cut prosthesis has been processed to form the concave luminal and abluminal surfaces and convex side surfaces. In another example the processing includes shaping by application of a solvent by at least one of dipping, spraying, or contact with a solvent vapor.

The endoprosthesis stent structures can include a plurality of circumferentially expandable serpentine rings, each serpentine ring including struts joined by crowns, wherein one strut joins two adjacent crowns of a serpentine ring, and wherein the crowns act as hinges allowing the struts to spread as the ring expands circumferentially, links joining some but not all crowns on adjacent serpentine rings. The treatment may modify the surfaces of all of the scaffold structures of the endoprosthesis.

In another embodiment, a polymer endoprosthesis includes a tubular expandable endoprosthesis body comprising a polymeric material which has been cut from a tube to form an endoprosthesis with a plurality of struts each having a luminal surface, an abluminal surface, and two side surfaces extending between said luminal and abluminal surfaces, wherein at least one of the luminal and abluminal surfaces is concave and the two side surfaces are convex In another embodiment, a method of forming a polymer endoprosthesis with modified surfaces includes the steps of forming a tubular expandable endoprosthesis with a plurality of struts each having a luminal surface, an abluminal surface and two side surfaces extending between said luminal and abluminal surfaces by cutting the endoprosthesis from a polymer tube and exposing the tubular expandable endoprosthesis to a treatment for a predetermined period of time to modify the surfaces, wherein the resulting modified luminal and abluminal surfaces are concave while the modified two side surfaces are convex.

In one embodiment, the Tg of the polymer comprised in the polymeric scaffold after the shaping process is substantially unchanged from before the treatment process.

In one embodiment, the crystallinity of the polymer comprised in the polymeric scaffold after the shaping process is substantially unchanged from before the treatment process.

In one embodiment, the molecular weight of the polymer comprised in the polymeric scaffold after the shaping process is substantially unchanged from before the treatment process.

In one embodiment, the molecular number of the polymer comprised in the polymeric scaffold after the shaping process is substantially unchanged from before the treatment process.

In one embodiment, the polydispersity index of the polymer comprised in the polymeric scaffold after the shaping process is substantially unchanged from before the treatment process.

In a further embodiment, a method of forming a polymer stent prosthesis with a controlled strut thickness includes the steps of forming a tubular expandable prosthesis with a plurality of struts by cutting the prosthesis from a polymer tube having a first thickness, said prosthesis comprising a polymeric material and exposing the tubular expandable prosthesis to a solvent for a predetermined period of time to redistribute said polymeric material without substantially dissolving it to adjust a thickness of the plurality of struts to a second thickness, wherein the second thickness is greater than the first thickness.

In a further embodiment, a polymer endoprosthesis includes a tubular expandable endoprosthesis body comprising a polymeric material which has been cut from a tube to form an endoprosthesis with a plurality of struts each having a luminal surface, an abluminal surface, and two side surfaces extending between said luminal and abluminal surfaces, wherein the abluminal surfaces of the struts are shaped to form concave surfaces extending substantially from one side surface to an opposite side surface; and a coating comprising at least one drug formed over at least some portions of the tubular expandable endoprosthesis body. In some embodiments the at least one drug coats all surfaces of the tubular expandable endoprosthesis body.

In another embodiment, a method of forming a polymer stent prosthesis with a modified shape includes the steps of forming a tubular expandable prosthesis with a plurality of struts having luminal, abluminal and side surfaces extending between said luminal and abluminal surfaces by cutting the prosthesis from a polymer tube having a first thickness and treating the tubular expandable endoprosthesis to increase a thickness of the plurality of struts between the luminal and abluminal surfaces while decreasing a width of the struts between the side surfaces by redistributing the polymer.

In one embodiment, the biodegradable stent prosthesis, comprises a tubular biodegradable polymeric material, said polymeric material is patterned into a stent capable of radial expansion from a crimped diameter to a deployed larger diameter, wherein the stent comprises a plurality of struts joined by crowns and at least some of the crowns are connected to adjacent crowns, wherein said patterned stent struts and crowns, each have a luminal surface, an abluminal surface, and two side surfaces extending between said luminal and abluminal surfaces, wherein at least some abluminal surfaces (optionally substantially all abluminal surfaces) have concave shapes across substantially the width of said abluminal surfaces, and at least some side surfaces (optionally substantially all side surfaces) have convex shapes across the thickness of said side surfaces, wherein the stent in the deployed diameter has sufficient strength to support a blood vessel.

In one embodiment, the biodegradable polymeric stent prosthesis, comprising a tubular biodegradable polymeric material, said polymeric material is patterned into a stent capable of radial expansion from a crimped diameter to a deployed larger diameter, wherein the stent comprises a plurality of struts joined by crowns and at least some of the crowns are connected to adjacent crowns, wherein said patterned stent struts and crowns each have a luminal surface, an abluminal surface, and two side surfaces extending between said luminal and abluminal surfaces, wherein at least some abluminal surfaces (optionally substantially all abluminal surfaces) have concave shapes across substantially the width of said abluminal surfaces, and at least some side surfaces (optionally substantially all side surfaces) have convex shapes across the thickness of said side surfaces, wherein the stent in the deployed diameter has sufficient strength to support a blood vessel.

In one embodiment, the biodegradable polymeric stent prosthesis, comprising a tubular biodegradable polymeric material, said polymeric material is patterned into a stent structure capable of radial expansion from a crimped diameter to a deployed larger diameter, wherein the stent structure comprises a plurality of struts joined by crowns and at least some of the crowns are connected to adjacent crowns, wherein said patterned stent structure struts and crowns each have a luminal surface, an abluminal surface, and two side surfaces extending between said luminal and abluminal surfaces, wherein at least some abluminal surfaces (optionally substantially all abluminal surfaces) have concave shapes across substantially the width of said abluminal surfaces, and at least some side surfaces (optionally substantially all side surfaces) have convex shapes across the thickness of said side surfaces, wherein the stent structure in the deployed diameter has sufficient strength to support a blood vessel.

In one embodiment, the biodegradable stent prosthesis, comprising a tubular biodegradable polymeric material, said polymeric material has a stent pattern, said stent capable of radial expansion from a crimped diameter to a deployed larger diameter, wherein the stent comprises a plurality of struts joined by crowns and at least some of the crowns are connected to adjacent crowns, wherein said stent struts and crowns each have a luminal surface, an abluminal surface, and two side surfaces extending between said luminal and abluminal surfaces, wherein at least some abluminal surfaces (optionally substantially all abluminal surfaces) have concave shapes across substantially the width of said abluminal surfaces, and at least some side surfaces (optionally substantially all side surfaces) have convex shapes across the thickness of said side surfaces, wherein the stent in the deployed diameter has sufficient strength to support a blood vessel.

In one embodiment, the biodegradable polymeric stent prosthesis, comprising a tubular biodegradable polymeric material, said polymeric material is patterned into a stent capable of radial expansion from a crimped diameter to a deployed larger diameter, wherein the stent comprises a plurality of struts joined by crowns and at least some of the crowns are connected to adjacent crowns, wherein said patterned stent struts and crowns each have a luminal surface, an abluminal surface, and two side surfaces extending between said luminal and abluminal surfaces, wherein at least some abluminal surfaces (optionally substantially all abluminal surfaces) have concave shapes, and at least some side surfaces (optionally substantially all side surfaces) have convex shapes, wherein the stent in the deployed diameter has sufficient strength to support a blood vessel.

In one embodiment, the biodegradable stent prosthesis, comprising a biodegradable polymeric material, said polymeric material is patterned into a stent capable of expansion from a crimped diameter to a deployed larger diameter, wherein the patterned stent comprises a plurality of struts, crowns, and optionally links connecting at least some adjacent crowns, wherein said patterned stent struts, crowns, and links each have a luminal surface, an abluminal surface, and two side surfaces extending between said luminal and abluminal surfaces, wherein at least some abluminal surfaces (optionally substantially all abluminal surfaces) have concave shapes across substantially the width of said abluminal surfaces, and at least some side surfaces (optionally substantially all side surfaces) have convex shapes across the thickness of said side surfaces, wherein the patterned stent in the deployed diameter has sufficient strength to support a blood vessel. In one embodiment, the polymeric material is formed as a tubular body.

In one embodiment, the biodegradable stent prosthesis, comprising a biodegradable polymeric material, said polymeric material is patterned into a stent capable of expansion from a crimped diameter to a deployed larger diameter, wherein the patterned stent comprises a plurality of struts, crowns, and optionally links connecting at least some adjacent crowns, wherein said patterned stent struts, crowns, and links each have a luminal surface, an abluminal surface, and two side surfaces extending between said luminal and abluminal surfaces, wherein at least some abluminal surfaces (optionally substantially all abluminal surfaces) have concave shapes along substantially the width of said abluminal surfaces, and at least some side surfaces (optionally substantially all side surfaces) have convex shapes along the thickness of said side surfaces, wherein the patterned stent in the deployed diameter has sufficient strength to support a blood vessel. In one embodiment, the polymeric material is formed as a tubular body.

In one embodiment, the biodegradable polymeric stent prosthesis, comprising a biodegradable polymeric material, said polymeric material formed as a tubular body and patterned into a stent capable of expansion from a crimped diameter to a deployed larger diameter, wherein the patterned stent comprises a plurality of struts joined by crowns wherein at least some adjacent crowns are connected, wherein said patterned stent struts and crowns, each have a luminal surface, an abluminal surface, and two side surfaces extending between said luminal and abluminal surfaces, wherein at least some abluminal surfaces are (optionally substantially all abluminal surfaces) have concave shapes across substantially the width of said abluminal surfaces, and at least some side surfaces (optionally substantially all side surfaces) have convex shapes across the thickness of said side surfaces, wherein the patterned stent in the deployed diameter has sufficient strength to support a blood vessel.

In one embodiment, the concave abluminal surfaces and convex side surfaces, substantially increases the surface area along the length of stent prosthesis, while reducing surface porosity of the luminal and side surfaces.

In one embodiment, the concave abluminal surfaces and convex side surfaces, substantially increases the surface area along the length of stent prosthesis, while substantially maintaining surface porosity of the luminal and side surfaces.

In one embodiment, the patterned stent expands from a crimped configuration to a larger expanded configuration substantially free from rotation of patterned stent struts, crowns, and optionally links.

In one embodiment, the patterned stent expands from a crimped configuration to a larger expanded configuration having rotation of patterned stent struts, crowns, and optionally links, less than 45 degrees.

In one embodiment, the biodegradable stent prosthesis, comprises a biodegradable polymeric material, said polymeric material is patterned into a stent capable of radial expansion from a crimped diameter to a deployed larger diameter, wherein the patterned stent comprises a plurality of struts joined by crowns wherein at least some adjacent crowns are connected, wherein said patterned stent struts and crowns each have a luminal surface, an abluminal surface, and two side surfaces extending between said luminal and abluminal surfaces, wherein the patterned stent is treated and at least some abluminal surfaces (optionally substantially all abluminal surfaces) are modified from being substantially convex shapes to becoming substantially concave shapes across substantially the width of said abluminal surfaces, and at least some side surfaces (optionally substantially all side surfaces) are modified from being substantially flat shapes to substantially convex shapes across the thickness of said side surfaces, wherein the patterned stent in the deployed diameter has sufficient strength to support a blood vessel.

In one embodiment, the biodegradable stent prosthesis, comprises a biodegradable polymeric material, said polymeric material is patterned into a stent capable of expansion from a crimped diameter to a deployed larger diameter, wherein the patterned stent comprises a plurality of struts joined by crowns wherein at least some adjacent crowns are connected, wherein said patterned stent struts and crowns each have a luminal surface, an abluminal surface, and two side surfaces extending between said luminal and abluminal surfaces, wherein the patterned stent is treated and at least some side surfaces (optionally substantially all side surfaces) are modified from being substantially flat shapes to substantially convex shapes across the thickness of said side surfaces, wherein the patterned stent in the deployed diameter has sufficient strength to support a blood vessel.

In one embodiment, the polymeric material is formed from a tubular body.

In another embodiment, the biodegradable prosthesis is a polymeric biodegradable prosthesis.

In one embodiment, the biodegradable polymeric stent prosthesis, comprises a biodegradable polymeric material, said polymeric material is patterned into a stent capable of radial expansion from a crimped diameter to a deployed larger diameter, wherein the patterned stent comprises a plurality of struts joined by crowns wherein at least some adjacent crowns are connected, wherein said patterned stent struts and crowns each have a luminal surface, an abluminal surface, and two side surfaces extending between said luminal and abluminal surfaces, wherein the patterned stent is treated and at least some side surfaces (optionally substantially all side surfaces) are modified to substantially convex shapes across the thickness of said side surfaces, wherein the patterned stent in the deployed diameter has sufficient strength to support a blood vessel.

In one embodiment, the biodegradable polymeric stent prosthesis comprises a biodegradable polymeric material, said polymeric material formed as a tubular body and patterned into a stent capable of expansion from a crimped diameter to a deployed larger diameter, wherein the patterned stent comprises a plurality of struts joined by crowns wherein at least some adjacent crowns are connected, wherein said patterned stent struts and crowns each have a luminal surface, an abluminal surface, and two side surfaces extending between said luminal and abluminal surfaces, wherein the patterned stent is treated and at least some abluminal surfaces (optionally substantially all abluminal surfaces) are modified to substantially concave shapes across substantially the width of said abluminal surfaces, and at least some side surfaces (optionally substantially all side surfaces) are modified to substantially convex shapes across the thickness of said side surfaces, wherein the patterned stent in the deployed diameter has sufficient strength to support a blood vessel.

In one embodiment, the treatment of the stent prosthesis to modify the abluminal surfaces to concave shapes and the side surfaces to convex shapes allows the polymeric material to flow from one surface to an adjacent surface.

In one embodiment, the treatment of the stent prosthesis to modify the abluminal surfaces to concave shapes and the side surfaces to convex shapes allows the polymeric material to flow from one surface to an adjacent surface without substantially dissolving the polymeric material.

In one embodiment, the treatment of the stent prosthesis to modify the abluminal surfaces to concave shapes and side surfaces to convex shapes allows the polymeric material to flow from one surface to an adjacent surface, without substantially changing the stent pattern.

In one embodiment, the treatment of the stent prosthesis to modify the abluminal surfaces to concave shapes and the side surfaces to convex shapes increases hydrophobicity of said surfaces, preferably by at least 15%, more preferably by at least 30%, most preferably by at least 50%.

In one embodiment, the treatment of the stent prosthesis to modify the abluminal surfaces to concave shapes and the side surfaces to convex shapes allows the polymeric material to flow from one surface to an adjacent surface.

In one embodiment, the treatment of the stent prosthesis to modify the abluminal surfaces to concave shapes and the side surfaces to convex shapes prevents said surfaces from rotating around their axis upon expansion of the stent prosthesis from a crimped configuration to an expanded larger configuration to support a blood vessel.

In one embodiment, the treatment of the stent prosthesis to modify the abluminal surfaces to concave shapes and the side surfaces to convex shapes allows the polymeric material to flow from one surface to an adjacent surface, without substantially changing the weight of the stent prosthesis.

In one embodiment, the biodegradable stent prosthesis is a polymeric biodegradable stent prosthesis. In another embodiment, the biodegradable polymeric stent prosthesis is substantially all comprised of polymeric material. In another embodiment, the polymeric biodegradable stent prosthesis is substantially all comprised of polymeric material and metallic radiopaque markers. In another embodiment, the polymeric biodegradable stent prosthesis is substantially all comprised of polymeric material and non-polymeric radiopaque markers. In another embodiment, the polymeric biodegradable stent prosthesis is substantially all comprised of polymeric material and some non-polymeric material.

In one embodiment, the treatment of the stent prosthesis to modify the abluminal surfaces to concave shapes or to a concave shape provides abluminal surfaces having a concave shape, but not necessarily identical concave shapes. Similarly, the treatment of the stent prosthesis to modify the side surfaces to convex shapes or to a convex shape provides side surfaces having a convex shape but not necessarily identical convex shapes. The resulting shapes may vary in radii of curvature and where on the strut, crown or link the mid-point of the curve occurs.

In one embodiment, the polymeric degradable stent is formed from a tubular body by extrusion, dipping, spraying, or printing, wherein the tubular body is formed and patterned at 1.1 to 1.5 times an intended deployed diameter of the stent (labeled nominal diameter), and treating the patterned stent to form concave shapes on at least some abluminal surfaces of the struts and crowns, and convex shapes on at least some side surfaces of said struts and crowns. The stent prosthesis is then coated with a drug and polymer matrix maintaining the concave abluminal surfaces and convex side surfaces, is then crimped onto a delivery system, packaged, and sterilized. Optionally the tube or stent is heated at a temperature ranging between 50 degrees and 150 degrees Celsius for between 1 minute and 5 hours, before patterning and/or after patterning, one or more times.

EXAMPLES

Example 1

Biodegradable polymer scaffolds made from polylactide based polymer were treated with a solvent of 4 parts dichloromethane (methylene chloride) and 6 parts ethanol for 5 seconds and rinsed with ethanol for 3 seconds. Both treated and non-treated scaffolds were then heat treated for 3 hours at 90 deg. C. They were coated with a drug matrix coating and sterilized by Ebeam. The scaffolds were tested for radial strength using an Instron connected to an iris based tester. Treated and untreated scaffolds were chosen based on their similarity in thickness and width to show the benefits of treatment in increasing strength for the same or similar strut profile. As shown in Table 1, the radial strength of the treated scaffolds with modified structure cross section of convex sides and concave luminal and abluminal surface were higher by at least 15% than the similarly sized scaffolds with substantially rectangular struts (non-treated).

TABLE 1

Summary of Radial Strength

|  | Strut Thickness | | Strut Width | | Radial Strength | |
|---|---|---|---|---|---|---|
|  | inches | micrometer | In | micrometer | (psi) | n |
| Treated | 0.0043 | 110 | 0.0074 | 188 | 13.7 | 3 |
| Non-Treated | 0.0046 | 116 | 0.0074 | 188 | 11.9 | 4 |

FIG. 2 shows a cross section of a scaffold strut after treatment. The scaffold cross section before treatment had substantially rectangular laser cut struts. The scaffold of FIG. 2 is shown before coating with drug matrix.

The strut after treatment has a narrower width and a slightly greater thickness as shown in Table 2 below.

TABLE 2

Summary of Dimension Changes with Treatment

|  | Strut Thickness | | Strut Width | |
|---|---|---|---|---|
|  | Inches | micrometers | Inches | micrometers |
| Before Treatment | 0.0032 | 81 | 0.0080 | 203 |
| After Treatment | 0.0043 | 116 | 0.0074 | 188 |

For the particular treatment process in this Example, the struts after treatment have convex side surfaces and have a slight concavity in the luminal and abluminal surfaces. The strut dimensions given in Table 2 are maximum dimensions for the width and thickness, taken at the widest or thickest spot on the strut. Although the maximum dimensions have been used, the minimum and mean dimensions can be used for dimensions. The minimum and mean dimensions also increased in the thickness direction and remained the same or decreased in the width direction. According to this example, the treatment resulted in a 43% increase in strut thickness and a 7% decrease in strut width.

A percent shape modification treatment, or amount of change in shape, can be calculated by measuring at one cross section the minimum strut width, generally at the luminal or abluminal surface of the strut ($W_{min}$) and the maximum strut width ($W_{max}$) which occurs near a midpoint between the luminal or abluminal surface of the strut and calculating percent treatment=$[1-(W_{min}-W_{max})] \times 100$ as shown in Table 3. In one embodiment, the percent shape modification treatment is at least 10%, or at least 20%, or at least 30% or at least 40%.

TABLE 3

Percent Treatment

|  | Ring 1 Strut Width (in) | | Middle Ring Strut Width (in) | |
|---|---|---|---|---|
| Unit # | Max | Min | Max | Min* |
| 3 × 28 mm | | | | |
| 1 | 0.0073 | 0.0035 | 0.0075 | 0.0048 |
| 2 | 0.0073 | 0.0043 | 0.0074 | 0.0045 |
| 3 | 0.0073 | 0.0044 | 0.0071 | 0.0045 |
| 4 | 0.0074 | 0.0042 | 0.0073 | 0.0041 |
| 5 | 0.0072 | 0.0045 | 0.0068 | 0.0031 |
| Average | 0.0073 | 0.0042 | 0.0072 | 0.0042 |

TABLE 3-continued

Percent Treatment

|  | Ring 1 Strut Width (in) | | Middle Ring Strut Width (in) | |
|---|---|---|---|---|
| Unit # | Max | Min | Max | Min* |
| Low | 0.0072 | 0.0035 | 0.0068 | 0.0031 |
| High | 0.0074 | 0.0045 | 0.0075 | 0.0048 |
| % shape modification Treatment | | | 43% | |
| 3 × 14 mm | | | | |
| 1 | 0.0071 | 0.0045 | 0.0071 | 0.0044 |
| 2 | 0.0071 | 0.0047 | 0.0069 | 0.0046 |
| 3 | 0.0078 | 0.0048 | | |
| Average | 0.0074 | 0.0047 | 0.0070 | 0.0045 |
| Low | 0.0071 | 0.0045 | 0.0069 | 0.0044 |
| High | 0.0078 | 0.0048 | 0.0071 | 0.0046 |
| % Treatment | | | 37% | |

The treated scaffolds of Example 1 were found to have no significant weight/mass change after treatment. This shows that the solvent is not removing polymer from the scaffolds, but is instead redistributing the polymer material to modify the shape of the surfaces. In this example, the difference in mass before and after treatment is less than 1%.

TABLE 4

Mass Before and After Treatment

| Before shape modification Treatment (mg) | |
|---|---|
| 1 | 5.212 |
| 2 | 5.309 |
| 3 | 5.337 |
| Mean | 5.286 |
| After shape modification Treatment (mg) | |
| 1 | 5.194 |
| 2 | 5.353 |
| 3 | 5.370 |
| 4 | 5.379 |
| 5 | 5.372 |
| Mean | 5.329 |
| % Difference | 0.81% |

Example 2

In another example, the side and abluminal surfaces of at least a portion of the struts, crowns, links and other scaffold structures can be shaped by solvent dipping while maintaining a substantially flat surface on the luminal side by inserting a tight mandrel such as a Teflon rod or tube inside the scaffold. The scaffold supported tightly on the mandrel is then dipped into a first solvent for about 1 second, 2 seconds, 3 seconds, or up to 20 seconds to cause the solvent to redistribute polymer material. The scaffold is quickly removed from the solvent when the desired shaping is achieved. Preferably the scaffold is rinsed in a second solvent to remove materials that are adhering to the scaffold and to fix the desired shape. FIG. 4 shows a cross sectional shape of a scaffold which can result from treatment by this process.

Although a tight fitting inner mandrel is described for blocking contact of the first solvent with the luminal side of the scaffold, other methods of masking the luminal side can also be used to prevent shaping of the luminal surfaces of the scaffold. Although the luminal surface of the scaffold without treatment are described as substantially flat surfaces, it should be understood that the scaffold if formed from a tube, have surfaces with some slight curvature corresponding to the curvature of the tube. Substantially flat surfaces can occur if the structure is formed from a sheet.

Example 3

Biodegradable polymer scaffolds made from polylactide based polymer were treated with a solvent based scaffold modification process described above to provide a structure cross section with convex sides and concave abluminal surface. The modification of the scaffold surface shapes was to provide improved tracking and/or push by reducing the force required to track or push the scaffold mounted on a catheter through a cylindrical body, such as a blood vessel. The reduction of track or push force is achieved by changing the area of surface contact between the modified scaffold shape and the vessel. On the abluminal side, the unmodified surfaces on the scaffold structure can act like ratchet elements as the scaffold is pushed through a blood vessel, especially one with calcified lesions. This may inhibit tracking through the vessel because the sides may get caught on the walls of the artery.

A test method was developed to characterize a force required for a scaffold delivery system to cross a lesion located at the apex of a curve in a test fixture with a curved track to simulate a blood vessel.

Figure 14:
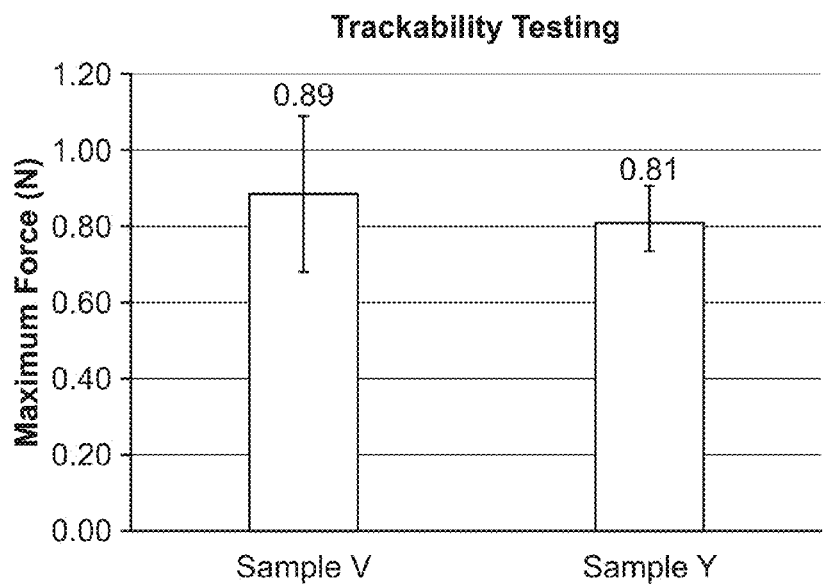
FIG. 14 is a graph of the results of trackability testing.

The fixture is immersed in a water bath maintained at 37° C. and the catheter with a mounted scaffold is pushed through the fixture. The push force is measured by the Instron attached to the catheter delivery system. The force is measured for units with scaffolds with no modification (sample V) and flat side surfaces and scaffolds with shape modification with convex side structures (sample Y). FIG. 14 shows a lower push force for the modified scaffold, indicating better trackability.

Example 4

A bioresorbable scaffold of 6.0 mm diameter and 60 mm in length is laser cut from a tube of 200 micron thickness made from a copolymer of polylactic acid-co-glycolide. The scaffold is mounted on a smaller mandrel rotating around its longer axis in an enclosed refrigerated chamber and is exposed to surface modification with dry ice blasting equipment.

The sandblasting nozzle is attached to a programmable robotic arm to propel particles along the selected portions of the scaffold crowns and axial struts. The dry ice blasting nozzle is aimed at the luminal surfaces to compact the treated surface and create the concave shape of these surfaces. The nozzle of the equipment is aimed at the corners at an angle of about 20 to about 160 degrees with respect to the strut side surfaces to achieve compaction of material at the side surfaces at the corners to provide convex side surfaces without removing significant amounts of material from other parts of the scaffold. As described herein, the scaffold can be either tightly mounted on a mandrel or loosely mounting on a mandrel depending on the location of the surfaces to be shaped. The scaffold can also be positioned inside a tube to shape at least a portion of the surfaces on the luminal surface of the scaffold.

Example 5

Figure 15:
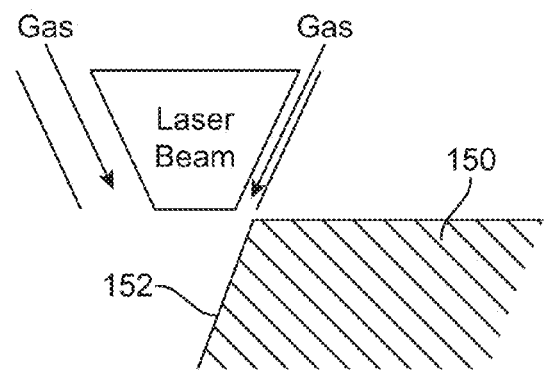
FIG. 15 is a schematic illustration of a laser process for creating convex side surfaces.

A bioresorbable scaffold of 3.5 mm diameter and 28 mm in length is laser cut from a tube of 100 micron thickness made from a polymer of polylactic acid based copolymer. A femtosecond laser is used to create convex and concave surface crowns on a scaffold. Because of the ability to ablate with low energy and cut layer by layer, a laser cutting program can be set to ablate about 25 or smaller micrometer width slots. As shown in FIG. 15, a series of overlapping cuts are made from the top surface to the edge of the scaffold structure 150 to achieve the desired shape on the crown, axial strut, or link. The scaffold structure can be cut with off-axis control such that the axis of laser beam and the axis of the assist gas supply nozzle on the laser such as a femtosecond laser is eccentrically oriented. This allows the laser to cut the scaffold material at an angle 152 rather than straight cut, eventually resulting in the convex cross section side surfaces.

Figure 16:
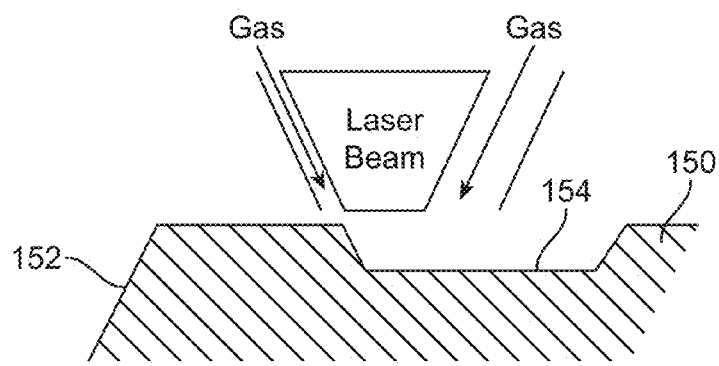
FIG. 16 is a schematic illustration of a laser process for creating concave luminal or abluminal surfaces.

FIG. 16 shows the process of the laser being used to create a concave surface on the luminal and/or abluminal surfaces by ablating the mid-section of the crown, strut or link 150 in stepwise cuts 154 in the surface of 150 to eventually create a concavity across substantially the width of the crown, strut or link.

Example 6

A multi-piece metal mold is created with fine scaffold negative features using wire EDM with the desired shaped strut features having convex sides and concave luminal and abluminal surfaces and held together under high pressure with holding clamps.

The equipment used is specifically designed to mold microparts with small plastic shot sizes for example a 3.5 mm×28 mm scaffold of 13 cubic millimeters, by utilizing high pressure of up to 100,000 psi and high speed to achieve injection times of around 0.01 seconds, to decrease the dwell time in the mold and minimize thermal degradation of the polymer. The strut width is 200 um and thickness is 200 um.

PLA based polymer is heated in the plasticizing portion of the machine, to the melt temperature of 200° C., and fed into the mold portion of the machine by the injector plunger.

After injection the mold is cooled rapidly to freeze the molten plastic and minimize thermal degradation, and the part removed. The scaffold structure has a cross section with the convex side surfaces and concave luminal and abluminal surfaces.

What is claimed is:

1. An expandable biodegradable stent prosthesis comprising:
 a biodegradable polymeric material which has been formed as a tubular body and patterned into a stent prosthesis comprising struts and crowns having luminal and abluminal surfaces; at least some of the struts and/or crowns cross sections have a convex shaped surface extending between the luminal and abluminal surfaces and at least some of the abluminal surfaces are concave across substantially the width of said surfaces; and wherein said stent prosthesis at body temperature is expandable from a crimped configuration to an expanded larger configuration, and having sufficient strength in the expanded configuration to support a body lumen.

2. An expandable biodegradable stent prosthesis comprising:
 a biodegradable polymeric material which has been formed as a tubular body and patterned into a stent radially expandable at body temperature from a crimped configuration to a deployed larger configuration, wherein the stent comprises a plurality of struts joined by crowns, wherein said struts and crowns each have a luminal surface, an abluminal surface, and two surfaces extending between the luminal and abluminal surfaces; and wherein at least some of the struts and/or crowns have a convex shape across substantially the thickness of said struts and/or crowns surfaces providing a dogbone shape extending between the luminal and abluminal surfaces; said stent prosthesis in the deployed configuration has sufficient strength to support a body lumen.

3. An expandable biodegradable stent prosthesis comprising:

a biodegradable polymeric material which has been formed as a tubular body and patterned into a stent radially expandable at body temperature from a crimped configuration to a deployed larger configuration, wherein the stent comprises a plurality of struts joined by crowns, wherein said struts and crowns each have a luminal surface, an abluminal surface, and two surfaces extending between the luminal and abluminal surfaces; and wherein the cross section of at least some of the struts and/or crowns have a convex shape across substantially the thickness of said struts and/or crowns surfaces and the intersections between the convex surface with the abluminal and luminal surfaces provide a thickness which is the greatest thickness of said struts and/or crowns; said stent prosthesis in the deployed configuration has sufficient strength to support a body lumen.

4. The expandable stent prosthesis of claim 1, 2, or 3, wherein the stent prosthesis body comprises a plurality of expandable rings, each ring is composed of struts joined by crowns, and each ring is connected to an adjacent ring by at least one link.

5. The expandable stent prosthesis of claim 4, wherein the prosthesis is expandable from a crimped diameter to a deployed diameter at body temperature without substantial rotation of the struts, crowns or links about their axis.

6. The expandable prosthesis of claim 1, wherein at least some of the struts and/or crowns cross sections have a dogbone shape.

7. The expandable stent prosthesis of claim 6 or 2, wherein said dog bone shape is not symmetrical.

8. The expandable prosthesis of claim 1, wherein the biodegradable polymeric material of said expandable stent prosthesis comprises at least two biodegradable polymers.

9. The expandable prosthesis of claim 1, wherein said surfaces have been treated to form the convex and concave surfaces.

10. The expandable stent prosthesis of claim 9, wherein the treatment includes laser shaping or shaping by application of a solvent by at least one of dipping, spraying, or contact with a solvent vapor.

11. The expandable stent prosthesis of claim 9, wherein the treatment includes shaping by tumbling, agitating, deburring, scraping, media blasting, laser treatment or heat treatment.

12. The expandable stent prosthesis of claim 9, wherein a mass of the expandable stent prosthesis after treatment is substantially the same as before treatment.

13. The expandable stent prosthesis of claim 9, wherein said prosthesis has been treated to redistribute material from the surface of some struts and/or crowns to an immediately adjacent surface of a strut and/or crown without a substantial change in body mass of said expandable stent prosthesis.

14. The expandable stent prosthesis of claim 9, said prosthesis has been treated to adjust a thickness of the struts and/or crowns from a first thickness before treatment to a second thickness after treatment, wherein the second thickness is greater than the first thickness.

15. The expandable stent prosthesis of claim 9, wherein the treatment causes a thickness of the struts and/or crowns between the luminal and abluminal surfaces to increase while a width of the struts and/or crowns between the convex surfaces remains substantially the same.

16. The expandable stent of claim 9, wherein the treatment comprises exposing the expandable prosthesis to a solvent for a predetermined period of time to provide substantially at least some convex surfaces between the luminal and abluminal surfaces and at least some concave abluminal surfaces of said struts and/or crowns.

17. The expandable stent prosthesis of claim 9, wherein the treatment causes a thickness of the plurality of struts and/or crowns between the luminal and abluminal surfaces to increase while decreasing a minimum width of the struts and/or crowns between the surfaces extending between the luminal and abluminal surfaces by redistributing the polymeric material.

18. The expandable prosthesis of claim 1, wherein the expandable stent prosthesis body has been patterned by a laser from a continuous tube substantially free from holes or other discontinuities.

19. The expandable stent prosthesis of claim 1, wherein the expandable stent prosthesis has been patterned from a tube by a laser and wherein the struts and/or crowns have been treated to form said concave abluminal surfaces and convex surfaces extending between the luminal and abluminal surfaces.

20. The expandable stent prosthesis of claim 1, further comprising a coating of at least one drug and at least one polymer formed over at least some portions of the expandable stent prosthesis body.

21. The expandable stent prosthesis of claim 1, further comprising a coating over the expandable stent prosthesis, said abluminal surfaces of said struts and/or crowns remaining substantially concave, and said surfaces extending between the luminal and abluminal surfaces of said struts and/or crowns remaining substantially convex.

22. The expandable prosthesis of claim 1, wherein the biodegradable polymeric material has an elastic modulus of at least 0.35 GPa.

23. The expandable stent prosthesis of claim 1, 2, or 3 wherein the biodegradable polymeric material comprises one or more of polymers and copolymers.

24. The expandable stent prosthesis of claim 1, 2 or 3 wherein the prosthesis is balloon expandable from a crimped diameter to a deployed diameter at body temperature without fracture.

25. The expandable stent prosthesis of claim 1, 2 or 3 wherein the biodegradable polymeric material comprises at least one material selected from the group consisting of lactides, poly-DL-Lactide, polylactide-co-gycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

26. The expandable stent prosthesis of claim 1, wherein biodegradable polymeric material has a molecular weight ranging from 100 KDa to 1000 KDa.

27. The expandable prosthesis of claim 1, wherein at least some of the luminal surfaces are concave across substantially the width of said surfaces and further comprising a coating over the expandable stent prosthesis, said luminal and abluminal surfaces of said struts and/or crowns remaining substantially concave, and said surfaces extending between the luminal and abluminal surfaces remaining substantially convex after coating.

28. The expandable stent prosthesis of claim 1, 2, or 3, further comprising biodegradable metal or metal alloy.

29. The expandable stent prosthesis of claim 1, 2, or 3, further comprising radiopaque markers.

30. The expandable stent prosthesis of claim 1, 2, or 3, wherein the abluminal and luminal surfaces of at least some of the struts and/or crowns are concave.

31. The expandable stent prosthesis of claim 1, 2, or 3, wherein the abluminal and luminal surfaces of at least some of the struts and/or crowns are concave across substantially the width of said surfaces.

32. The expandable stent prosthesis of claim 1, 2 or 3, further comprising a coating over at least a portion of said stent prosthesis, said coating contours to the shape of the surfaces without substantially changing the shape of the surfaces, wherein the biodegradable polymeric material has an elastic modulus of at least 0.35 GPa and comprises one or more of polymers and copolymers.

33. The expandable stent prosthesis of claim 1, 2, or 3, wherein said stent prosthesis has been heated one or more times before or after being patterned.

34. The expandable stent prosthesis of claim 1, further comprising a coating over at least a portion of the expandable stent prosthesis, said coating contours to the shape of the surfaces without substantially changing the shape of the surfaces, wherein the intersections between the convex surface with the abluminal and luminal surfaces provides a thickness which is the greatest thickness of said struts and/or crowns.

35. The expandable stent prosthesis of claim 1, 2 or 3, wherein the stent prosthesis comprises a plurality of struts joined by crowns, and at least some crowns are connected to adjacent crowns by a link.

36. The expandable stent prosthesis of claim 1, 2, or 3, wherein the biodegradable polymeric material has a Tg between 20° C. and 50° C.

37. The expandable biodegradable stent prosthesis of claim 2, wherein at least some of the struts and/or crowns abluminal surfaces have a concave shape across substantially the width of said struts and/or crowns abluminal surfaces.

38. The expandable biodegradable stent prosthesis of claim 2, wherein substantially all of the surfaces joining the luminal and abluminal surfaces have a convex shape across substantially the thickness between the luminal and abluminal surfaces.

39. The expandable biodegradable stent prosthesis of claim 2, wherein said prosthesis has been treated by contact with a solvent to provide said convex surfaces and dogbone shape.

40. The expandable biodegradable stent prosthesis of claim 2, wherein said prosthesis has been treated by contact with a solvent to redistribute said polymeric material to provide an increased thickness of said surfaces extending between the luminal and abluminal surfaces and decreased width of said abluminal and luminal surfaces.

41. The expandable biodegradable stent prosthesis of claim 2, wherein the thickness of at least some struts and/or crowns extending between the luminal and abluminal surfaces is variable across the width, continuously increasing in thickness towards the two ends of the abluminal surface.

42. The expandable stent prosthesis of claim 3, wherein the stent prosthesis further comprising a drug coating over at least a portion of the expandable stent prosthesis, said coating contours to the shape of the surfaces without substantially changing the shape of the surfaces, wherein the biodegradable polymeric material has an elastic modulus of at least 0.35 GPa and comprises one or more of polymers and copolymers.

* * * * *